United States Patent [19]

Michel et al.

[11] Patent Number: 4,537,770

[45] Date of Patent: Aug. 27, 1985

[54] A41030 ANTIBIOTICS

[75] Inventors: Karl H. Michel; Ralph E. Kastner, both of Indianapolis, Ind.

[73] Assignee: Eli Lilly and Company, Indianapolis, Ind.

[21] Appl. No.: 662,464

[22] Filed: Oct. 18, 1984

Related U.S. Application Data

[63] Continuation of Ser. No. 443,496, Nov. 22, 1982, abandoned, which is a continuation-in-part of Ser. No. 361,301, Mar. 24, 1982, abandoned.

[51] Int. Cl.$^3$ .................... A61K 35/00; C07C 103/52; C07G 7/00
[52] U.S. Cl. ............................ 424/118; 260/112.5 R; 260/112 R
[58] Field of Search ................. 424/118; 260/112.5 R, 260/112 R

[56] References Cited

U.S. PATENT DOCUMENTS

| | | | |
|---|---|---|---|
| 3,067,099 | 12/1962 | McCormick | 167/65 |
| 3,338,786 | 8/1967 | Kunstmann et al. | 167/65 |
| 3,952,095 | 4/1976 | Hamill et al. | 424/118 |
| 4,115,552 | 9/1978 | Hamill et al. | 424/118 |
| 4,239,751 | 12/1980 | Coronelli et al. | 424/118 |
| 4,322,343 | 3/1982 | Debono | 260/112.5 R |
| 4,322,406 | 3/1982 | Debono et al. | 424/118 |

FOREIGN PATENT DOCUMENTS 765886  1/1957  United Kingdom .

OTHER PUBLICATIONS

Williamson et al., "Structure Revision of the Antibiotic Vancomycin. The Use of Nuclear Overhauser Effect Difference Spectroscopy", *J. Am. Chem. Soc. 103*, 6580–6585, 1981.

Kalman et al., "An NMR Study of the Antibiotic Ristocetin A. The Negative Nuclear Overhauser Effect in Structure Elucidation", *J. Am. Chem. Soc.* 102, 897–905 (1980).

Ellestad et al., "Avoparcin and Epiavoparcin", *J. Am. Chem. Soc.* 103, 6522–6524 (1981).

Derwent Abstract 83-840048/50 of West German OLS 3320-342-A (Gruppo Lepetit SPA).

Hunt et al., "Structure of the Major Glycopeptide of the Teicoplanin Complex", *J. Amer. Chem. Soc.* 106, 4891–4895 (1984).

Barna et al., "Structure Elucidation of the Teichoplanin Antibiotics", *ibid* 106, 4895–4902 (1984).

*Primary Examiner*—Delbert R. Phillips
*Attorney, Agent, or Firm*—Nancy J. Harrison; Arthur R. Whale

[57] ABSTRACT

Antibiotic A41030, a complex of 7 individual factors, is produced by submerged, aerobic fermentation of new *Streptomyces virginiae* NRRL 12525, and *Streptomyces virginiae* NRRL 15156. The antiobiotic factors are separated and possess antibacterial activity against Staphylococcus and Streptococcus species which are penicillin resistant. In addition, the antibiotic factors have shown inhibition of *Streptococcus pneumonia* Park I. The complex and the individual factors enhance feed efficiency in ruminant animals, and are growth promoters in chickens and swine, and are especially valuable in milk production in dairy cattle.

7 Claims, 7 Drawing Figures

A41030 ANTIBIOTICS

CROSS REFERENCE

This application is a continuation of application Ser. No. 443,496, filed 11-22-82, which in turn is a continuation-in-part of application Ser. No. 361,301, filed Mar. 24, 1982, both now abandoned.

SUMMARY OF THE INVENTION

This invention relates to antibiotic A41030 complex comprising several factors, including individual factors A, B, C, D, E, F, and G. This complex is produced by culturing either one of two hitherto undescribed microorganisms, namely, *Streptomyces virginiae* NRRL 12525, and *Streptomyces virginiae* NRRL 15156, or an A41030-producing mutant or variant of each microorganism, under submerged aerobic fermentation conditions.

The A41030 antibiotics inhibit the growth of certain pathogenic microorganisms, in particular, those within the gram-positive genera Staphylococcus and Streptococcus which are resistant to penicillin. The antibiotics of this invention act to promote growth and improve feed efficiency in ruminant animals, poultry and swine, and other livestock, and to improve milk production in ruminant animals.

This invention also relates to a biologically-pure culture of *Streptomyces virginiae* NRRL 15156, useful for the production of A41030 antibiotics.

DESCRIPTION OF THE DRAWINGS

Infrared absorption spectra of A41030 factors A, B, C, D, E, F, and G are presented in the drawings as follows.

DETAILED DESCRIPTION OF THE INVENTION

Figure 1:
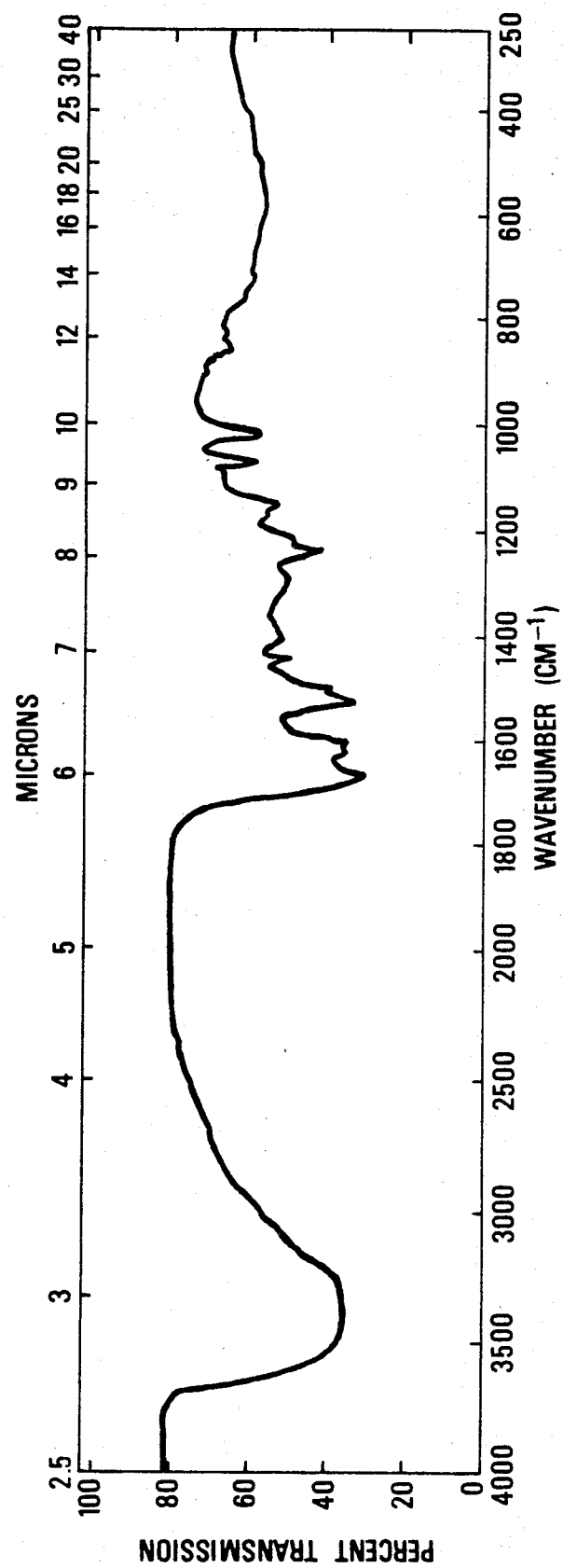
FIG. 1—A41030 factor A (in KBr pellet)
FIG. 2—A41030 factor B (in KBr pellet)
FIG. 3—A41030 factor C (in KBr pellet)
FIG. 4—A41030 factor D (in KBr pellet)
FIG. 5—A41030 factor E (in KBr pellet)
FIG. 6—A41030 factor F (in KBr pellet)
FIG. 7—A41030 factor G (in KBR pellet)

This invention relates to antibiotic substances. In particular, it relates to an antibiotic complex comprising several factors, including individual factors A, B, C, D, E, F, and G. This complex is produced by culturing hitherto undescribed microorganism, *Streptomyces virginiae* NRRL 12525, or hitherto undescribed microorganisms, *Streptomyces virginiae* NRRL 15156. For convenience in our laboratories, culture NRRL 15156 has been designated as culture A41030, and culture NRRL 12525 has been designated as culture A41030.4.

This invention also relates to a biologically-pure culture of *Streptomyces virginiae* NRRL 15156.

The term "complex", as used in the fermentation art, and in this specification, refers to a mixture of coproduced individual antibiotic factors. As will be recognized by those familiar with antibiotic production by fermentation, the number and ratio of the individual factors produced in an antibiotic complex will vary, depending upon the fermentation conditions and the strain used.

Culture A41030, identified as a strain of *Streptomyces virginiae*, was initially isolated from a soil sample collected in Indianapolis, Ind., and has been deposited and made a part of the stock culture collection of the Northern Regional Research Center, U.S. Separtment of Agriculture, Agricultural Research Service, Peoria, Ill. 61604, from which it is available to the public under the number NRRL 15156.

Culture A41030.4, which is a chemically-induced mutant of a strain of the *Streptomyces virginiae* culture A41030, has also been deposited and made a part of the stock culture collection of the Northern Regional Research Center, U.S. Department of Agriculture, Agricultural Research Service, Peoria, Ill. 61604, from which it is available to the public under the number NRRL 12525. Culture A41030.4 is claimed in companion application Ser. No. 361,302, filed Mar. 24, 1982.

Culture A41030 is classified as a strain of *Streptomyces virginiae*, and culture A41030.4 is classified as a chemically-induced mutant of a strain of *Streptomyces virginiae*, based upon a simultaneous culturing of A41030 and A41030.4; *Streptomyces avidinii* ATCC 27419; *Streptomyces columbiensis* ATCC 27425; *Streptomyces goshikiensis* ATCC 23914; *Streptomyces griseolavendus* ATCC 25457; *Streptomyces lavendulae* ATCC 8664; *Streptomyces toxytricini* ATCC 19813; and *Streptomyces virginiae*, Grundy, Whitman, Rdzok, Hanes and Sylvester 1952, ATCC 19817. The methods and media recommended by Shirling and Gottlieb ["Methods of Characterization of Streptomyces species," *Int. J. Syst. Bacteriol.* 16(3), 313–340 (1966)], along with certain supplementary tests were used. Culture A41030 and culture A41030.4 were also compared with published descriptions of the above-named strains appearing in "Bergey's Manual of Determinative Bacteriology" (8th Edition, edited by R. E. Buchanan and N. E. Gibbons, The Williams and Wilkins Co., Baltimore, Md.); and by Shirling and Gottlieb, "Cooperative Description of Type Strains of Streptomyces", *Int. J. Syst. Bacteriol.* 18(2), 178 (1968).

CHARACTERIZATION OF A41030 CULTURE AND OF A41030.4 CULTURE Morphology

A41030 produces well-developed aerial mycelia and sporophores which are both coiled and exhibit hooks and loops. A41030 is placed in the Spirales (S) section of Pridham et al., "A Guide for the Classification of Streptomycetes According to Selected Groups", *Appl. Microbiol.* 6, 52–79 (1957), as a primary morphology type, and in the Retinaculum-Apertum (RA) section of Pridham et al. as a secondary morphology type.

A41030.4 produces no aerial mycelia and no spores.

Cultural Characteristics

The growth characteristics of culture A41030, culture A41030.4, and S. virginiae ATCC 19817 on various media are presented in the following Table 1.

Color names were assigned according to the ISCC-NBS Centroid Color Charts Standard Sample No. 2106 (National Bureau of Standards, U.S. Department of Commerce, 1958), and the Color Harmony Manual, 4th Edition (Color Standards Department, Container Corporation of America, Chicago, Ill., 1958).

TABLE 1

Cultural Characteristics of A41030, A41030.4, and ATCC 19817

| Medium | | A41030 | A41030.4 | ATCC 19817 |
|---|---|---|---|---|
| ISP No. 2 | G | Abundant | Good | Abundant |
| | R | 72.d.OY | 90.gy.Y | 75.deep yBr |
| | Am | Abun:63.1.brGY | None | Abun:63.1.brGY |
| | Sp | None | None | None |
| ISP | G | Good | Poor | Fair |

TABLE 1-continued

| | | Cultural Characteristics of A41030, A41030.4, and ATCC 19817 | | |
|---|---|---|---|---|
| Medium | | A41030 | A41030.4 | ATCC 19817 |
| No. 3 | R | 93.yGray | 93.yGray | 90.gy.Y |
| | AM | Good:63.1.brGY | None | Fair:63.1.brGY |
| | Sp | None | None | None |
| ISP | G | Abundant | Poor | Good |
| No. 4 | R | 89.p.Y | 89.p.Y | 91.d.gy.Y |
| | Am | Abun:63.1.brGY | None | Good:63.1.brGY |
| | Sp | None | None | None |
| ISP | G | Abundant | Poor | Good |
| No. 5 | R | 89.p.Y | 89.p.Y | 89.p.Y |
| | Am | Abun:22.rGY | None | Good:63.1.brGY |
| | Sp | None | None | None |
| Czapek's agar | G | Fair | Not grown | Poor |
| | R | 264.1.Gray | — | 264.1.Gray |
| | Am | Poor:10.pKGY | — | Poor:10.pKGY |
| | Sp | None | — | None |
| TPO | G | Abundant | Good | Abundant |
| | R | 72.d.OY | 54.brO | 75.deep yBr |
| | Am | Abun:63.1.brGY | None | Abun:63.1.brGY |
| | Sp | None | None | None |

G = growth
R = reverse
Am = *aerial mycelia*
Sp = soluble pigment

A comparison of the carbon utilization patterns of culture A41030, of culture A41030.4, and of *Streptomyces virginiae* ATCC 19817 was conducted using ISP No. 9 basal medium to which filter-sterilized carbon sources were added to equal a final concentration of 1.0%. Plates were read after fourteen days incubation at 30° C. The results are set forth in Table 2, which follows:

TABLE 2

| CARBON UTILIZATION PATTERNS OF A41030, OF A41030.4, AND *STREPTOMYCES VIRGINIAE* ATCC 19817 | | | |
|---|---|---|---|
| Carbon Source | A41030 | A41030.4 | ATCC 19817 |
| Acetate-Na | — | — | — |
| D-Arabinose | — | — | — |
| L-Arabinose | — | — | — |
| Cellobiose | + | + | + |
| D-Fructose | ± | — | ± |
| D-Galactose | + | + | — |
| D-Glucose | + | + | + |
| i-Inositol | — | — | — |
| Lactose | — | — | — |
| D-Maltose | + | + | + |
| D-Mannitol | — | — | — |
| Melibiose | — | — | — |
| Raffinose | — | — | — |
| Rhamnose | — | — | — |
| D-Ribose | + | — | + |
| Salicin | + | ± | + |
| Succinate-Na | + | ± | + |
| Sucrose | — | — | — |
| D-Xylose | — | — | — |

Key:
− = no utilization
+ = utilization
± = partial utilization

Cell wall composition

Using hydrolyzed whole cells of the novel microorganisms, the isomers of diaminopimelic acid were determined according to the method of Becker et al., Appl. Microbiol. 11, 421–423 (1964). The results of this study are set forth below.

| Test | Result Observed |
|---|---|
| Isomers of 2,6- diaminopimelic acid | LL-isomer |

The similarities and differences of culture A41030 and culture A41030.4, as compared to *Streptomyces virginiae* ATCC 19817, are set forth in Table 3, which follows. Color names are assigned as described above, and the morphology as set forth in Pridham et al., supra.

TABLE 3

| Similarities and Differences of A41030, A41030.4, and *S. virginiae* ATCC 19817 | | | |
|---|---|---|---|
| Character | A41030 | A41030.4 | ATCC 19817 |
| Aerial spore color | GY | none | GY |
| Carbon utilization | + | + | + |
| (galactose) | + | + | — |
| (fructose) | + | — | + |
| (ribose) | + | — | + |
| Gelatin liquefaction | + | — | + |
| Melanin production | + | + | + |
| ISP No. 1 | + | + | — |
| ISP No. 6 | + | + | + |
| ISP No. 7 | — | — | — |
| Morphology | (RA) (S) | none | (RA) (S) |
| NaCl tolerance percent | 4 | 3 | 5 |
| Nitrate reduction | — | — | — |
| Optimum growth medium* | + | — | + |
| Reverse color | p.Y | p.Y | p.Y |
| Skim milk | + | + | + |
| Soluble pigment | — | — | — |
| Spore shape | oblong | none | oblong |
| Spore surface | smooth | none | smooth |
| Starch hydrolysis | — | — | — |
| Temperature range °C. | 10–37 | 10–34 | 15–37 |

*Tomato paste oatmeal agar slant medium

The antibiotic substances of this invention are arbitrarily designated herein as A41030 antibiotics. The A41030 complex contains several individual factors which are designated A41030 factors A, B, C, D, E, F, and G. In discussions of utility, the term "A41030 antibiotic" will be used, for the sake of brevity, to denote a member selected from the group consisting of A41030 complex, and A41030 factors A, B, C, D, E, F, and G.

The seven antibiotic factors are recovered from the fermentation and are obtained as a mixture, the A41030 complex. It will be recognized that the ratio of the factors in the A41030 complex will vary, depending upon the fermentation conditions used. The individual factors A, B, C, D, E, F, and G are separated and isolated as individual compounds, as hereinafter described. The A41030 complex is soluble in water, dilute aqueous acid, dilute aqueous base, methanol-water mixtures, ethanol-water mixtures, dimethylformamide and dimethylformamide-water mixtures, dimethylsulfoxide, dimethylsulfoxide-water mixtures, acetonitrile, acetone, ethyl acetate, tetrahydrofuran, methylene chloride, and the like.

The following paragraphs describe the physical and spectral properties of the A41030 factors which have thus far been characterized.

A41030 FACTOR A

Antibiotic A41030 factor A is a white, crystalline solid. Elemental analysis of A41030 factor A indicates that it has the following approximate percentage composition: 56.44% carbon, 3.58% hydrogen, 8.11% nitrogen, 23.20% oxygen, and 8.29% chlorine. As determined by field desorption and plasma desorption mass spectrometry, A41030 factor A has a molecular weight of 1231. Based on the elemental analysis and the molecular weight, an empirical formula of $C_{58}H_{44}Cl_3N_7O_{18}$ is assigned to factor A. Electrometric titration of factor A in 66% dimethylformamide in water indicated the presence of three titratable groups having $pK_a$ values of about 5.53, 7.60 and 10.37, with possibly additional $pK_a$'s>10.5 (initial pH 7.83). Antibiotic A41030 factor A has the following specific rotation: $[\alpha]_D^{25} - 19.6$ (c, 9.0 in dimethylsulfoxide).

The infrared absorption spectrum of A41030 factor A in KBr pellet is shown in the accompanying drawings as FIG. 1. The following distinguishable absorption maxima are observed: 3448-3226 (strong, broad), 1653 (strong), 1610 (weak), 1587 (medium), 1515 (strong), 1488 (weak), 1429 (medium), 1227 (strong), 1139 (medium), 1064 (strong), and 1010 (strong) cm$^{-1}$.

The ultraviolet absorption maxima of A41030 factor A in methanol:water (1:1) under acid, neutral, and basic conditions are recorded in Table 4.

Antibiotic A41030 factor A is soluble in alcohol-water mixtures, in dimethylsulfoxide, in dimethylformamide, in dimethylsulfoxide-water mixtures, in dimethylformamide-water mixtures, in dilute aqueous acid, and in dilute aqueous base.

On the basis of the observed physical chemical data, the following structure has been assigned to A41030 factor A.

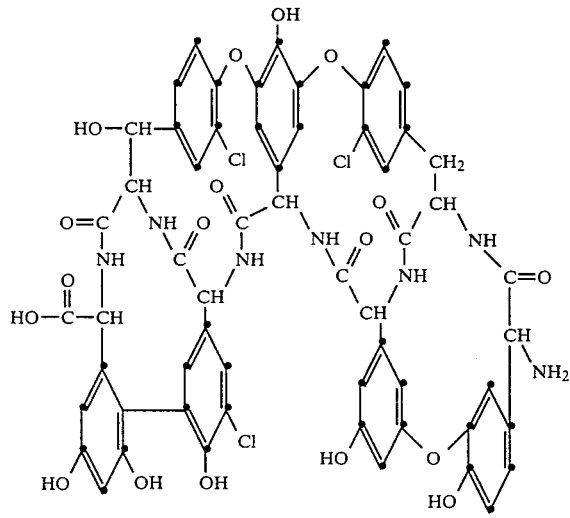

Using a biological assay and high performance liquid chromatography analysis, it has been found that factor A accounts for from about 94 to about 96% by weight of the antibiotic factors produced by culture A41030.4, with factors B, C, D, E, F, and G accounting for the remaining about 4 to about 6% by weight of the factors produced.

A41030 FACTOR B

Antibiotic A41030 factor B is a white solid, having an approximate elemental analysis as follows: 58.54% carbon, 4.21% hydrogen, 8.63% nitrogen, 5.96% chlorine, and by difference, 22.66% oxygen. Electrometric titration of factor B in 66% dimethylformamide in water indicated the presence of two titratable groups at $pK_a$ values of about 5.6 and 7.5, respectively, with possibly additional $pK_a$'s>10 (initial pH 6.22). An observed molecular weight of about 1197 was obtained using fast atom bombardment mass spectrometry. Based on elemental analysis and the observed molecular weight, an empirical formula of $C_{58}H_{45}Cl_2N_7O_{18}$ is assigned to factor B.

Figure 2:
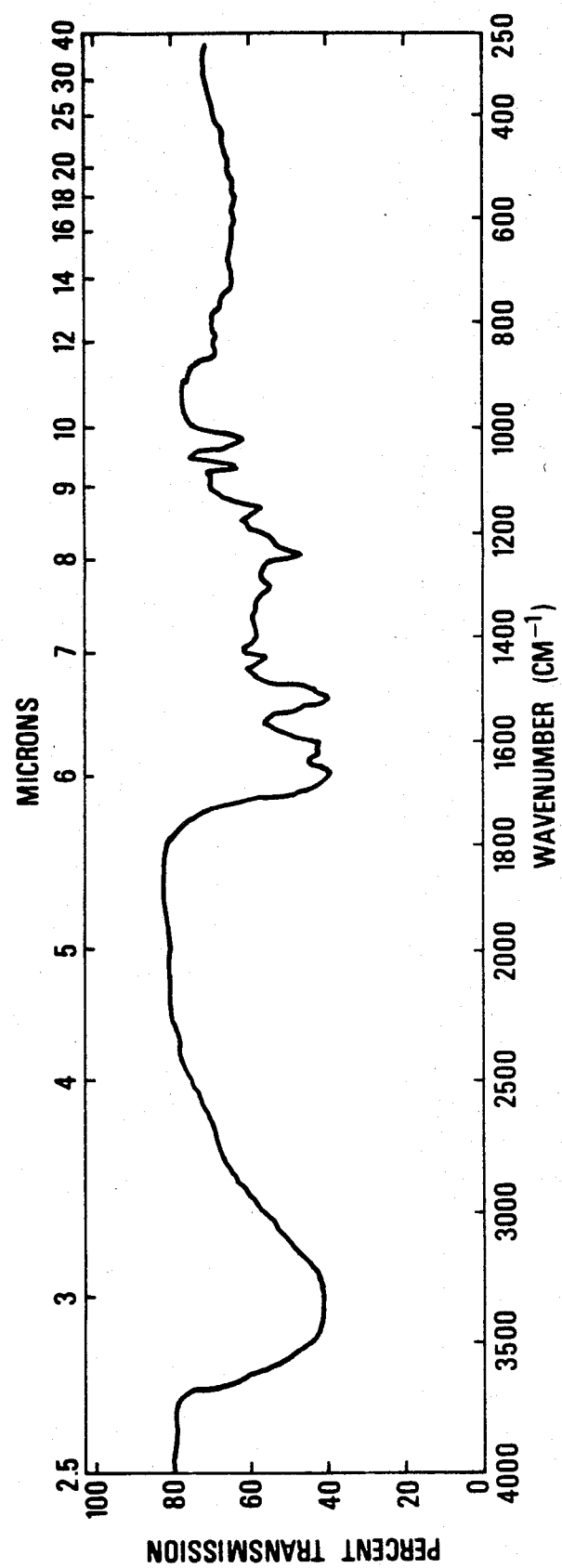

The infrared absorption spectrum of antibiotic A41030 factor B in KBr pellet is shown in the accompanying drawings as FIG. 2. The following distinguishable absorption maxima are observed: 3448-3226 (strong, broad), 1653 (strong), 1610 (medium), 1587 (weak), 1515 (strong), 1488 (weak), 1429 (medium), 1290 (weak), 1227 (strong), 1139 (medium), 1064 (strong), and 1010 (strong) cm$^{-1}$.

The ultraviolet absorption maxima of A41030 factor B in neutral, acidic, and basic methanol:water (1:1) are recorded in Table 4.

Antibiotic A41030 factor B is soluble in the same solvents as factor A.

On the basis of the observed physical chemical data, the following structure has been assigned to A41030 factor B.

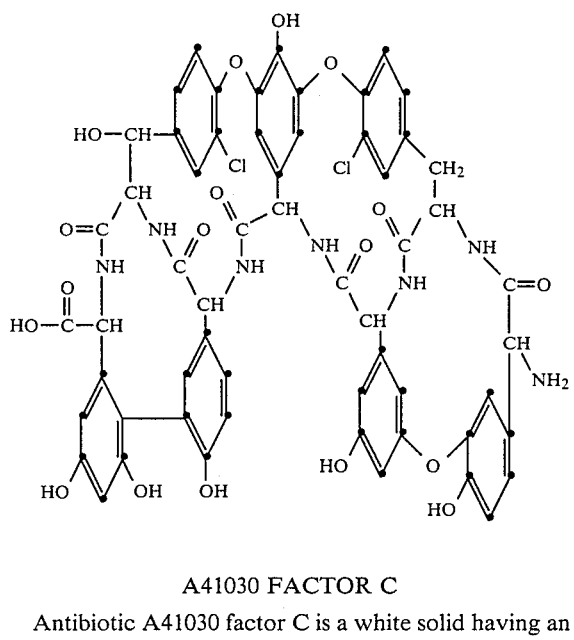

A41030 FACTOR C

Antibiotic A41030 factor C is a white solid having an approximate elemental analysis as follows: 48.87% carbon, 4.39% hydrogen, 6.16% nitrogen, 6.96% chlorine, and 33.81% oxygen. Electrometric titration of factor C in 66% dimethylformamide in water indicated the presence of two titratable groups at $pK_a$ values of about 5.5 and 7.1, respectively, with possibly additional $pK_a$'s>10 (initial pH 6.6). An observed molecular weight of about 1393 was obtained using fast atom bombardment mass spectrometry. Based on elemental analysis and the observed molecular weight, an empirical formula of $C_{64}H_{54}Cl_3N_7O_{23}$ is assigned to factor C.

Figure 3:
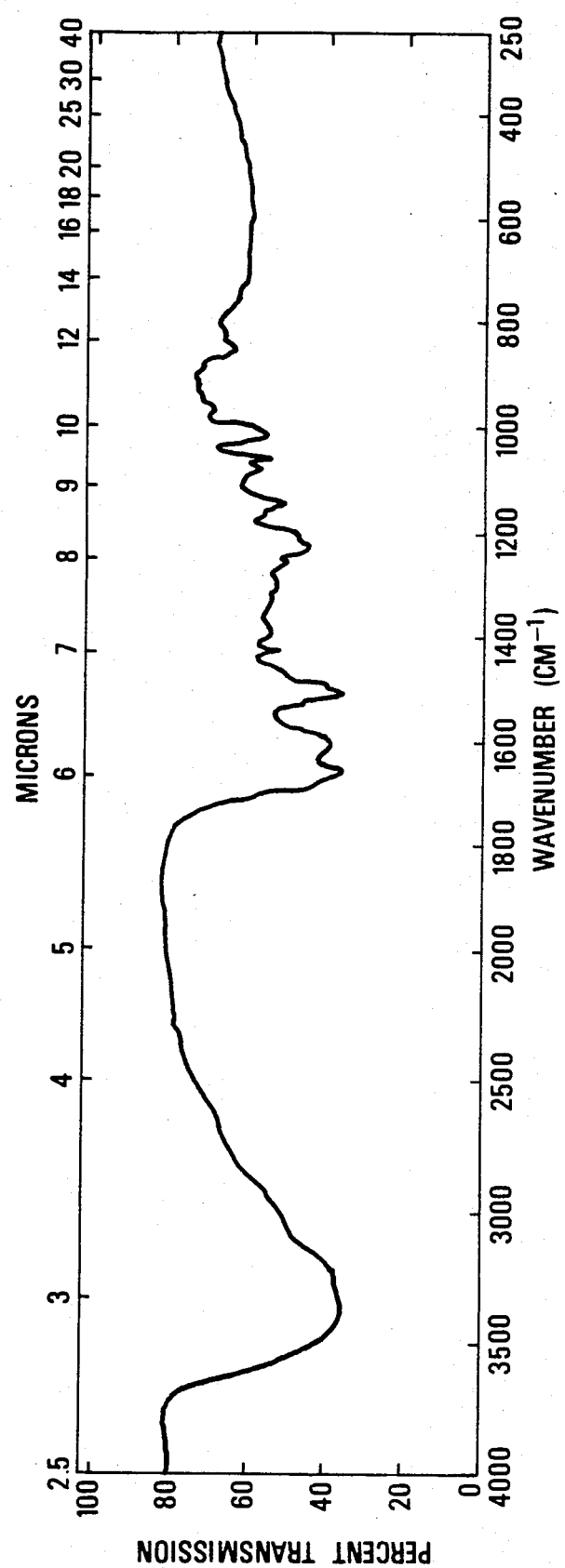

The infrared absorption spectrum of antibiotic A41030 factor C in KBr pellet is shown in the accompanying drawings as FIG. 3. The following distinguishable absorption maxima are observed: 3448-3226 (strong, broad), 1653 (strong), 1610 (medium), 1587 (weak), 1504 (strong), 1481 (weak), 1429 (medium), 1220 (strong), 1136 (strong), 1064 (weak), 1053 (medium), and 1005 (strong) cm$^{-1}$.

The ultraviolet absorption maxima of A41030 factor C in neutral, acidic, and basic methanol:water (1:1) are recorded in Table 4.

Antibiotic A41030 factor C is soluble in the same solvents as factor A.

On the basis of the observed physical chemical data, the structure of A41030 factor C is believed to be as follows:

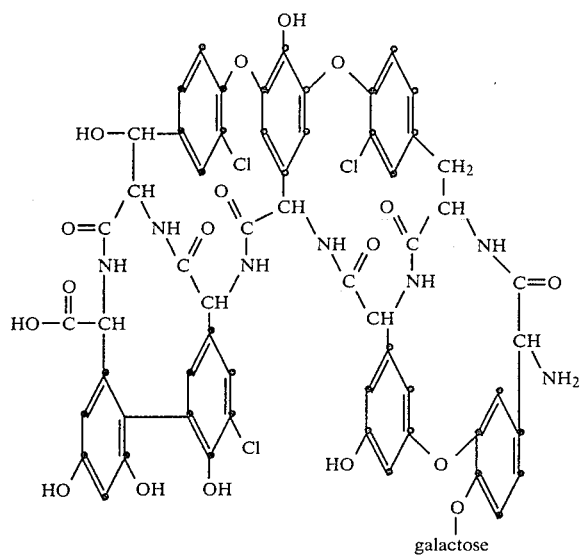

A41030 FACTOR D

Antibiotic A41030 factor D is a white, amorphous solid having an approximate elemental analysis as follows: 54.46% carbon, 4.35% hydrogen, 7.58% nitrogen, 4.27% chlorine, and by difference, 29.34% oxygen. Electromagnetic titration of factor D in 66% dimethylformamide in water indicated the presence of two titratable groups at $pK_a$ values of about 5.5 and 7.6, respectively, with possibly additional $pK_a$'s > 10 (initial pH 6.83). An observed molecular weight of about 1326 was obtained using fast atom bombardment mass spectrometry.

Figure 4:
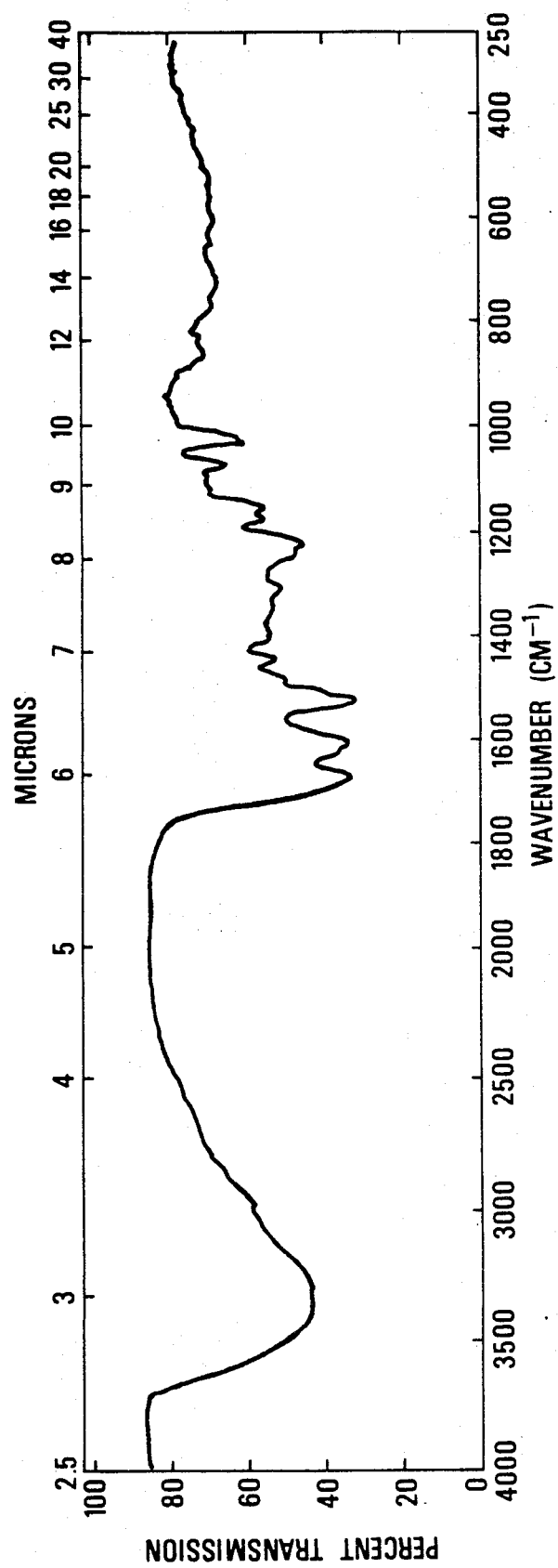

The infrared absorption spectrum of antibiotic A41030 factor D in KBr pellet is shown in the accompanying drawings as FIG. 4. The following distinguishable absorption maxima are observed: 3448–3226 (strong, broad), 2959 (weak), 1661 (strong), 1592 (strong), 1511 (strong), 1429 (weak), 1290 (weak), 1227 (weak), 1212 (medium), 1163 (weak), 1143 (weak), 1053 (medium), and 1010 (strong) cm$^{-1}$.

The ultraviolet absorption maxima of A41030 factor D in neutral, acidic, and basic methanol:water (1:1) are recorded in Table 4.

Antibiotic A41030 factor D is soluble in the same solvents as factor A.

On the basis of the observed physical chemical data, the structure of A41030 factor D is believed to be as follows:

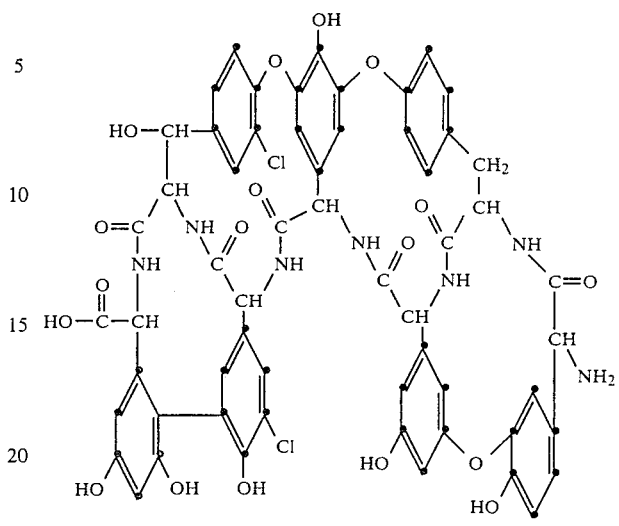

plus one or more n-butyl groups.

A41030 FACTOR E

Antibiotic A41030 factor E is a white solid having an approximate elemental analysis as follows: 56.06% carbon, 4.06% hydrogen, 8.53% nitrogen, 3.50% chlorine, and by difference, 27.85% oxygen. Electrometric titration of factor E in 66% dimethylformamide in water indicated the presence of two titratable groups at $pK_a$ values of about 5.8 and 7.7, respectively, with possibly additional $pK_a$'s > 10 (initial pH 6.57). An observed molecular weight of about 1163 was obtained using fast atom bombardment mass spectrometry. A tentative empirical formula of $C_{58}H_{46}ClN_7O_{18}$ is assigned to factor E.

Figure 5:
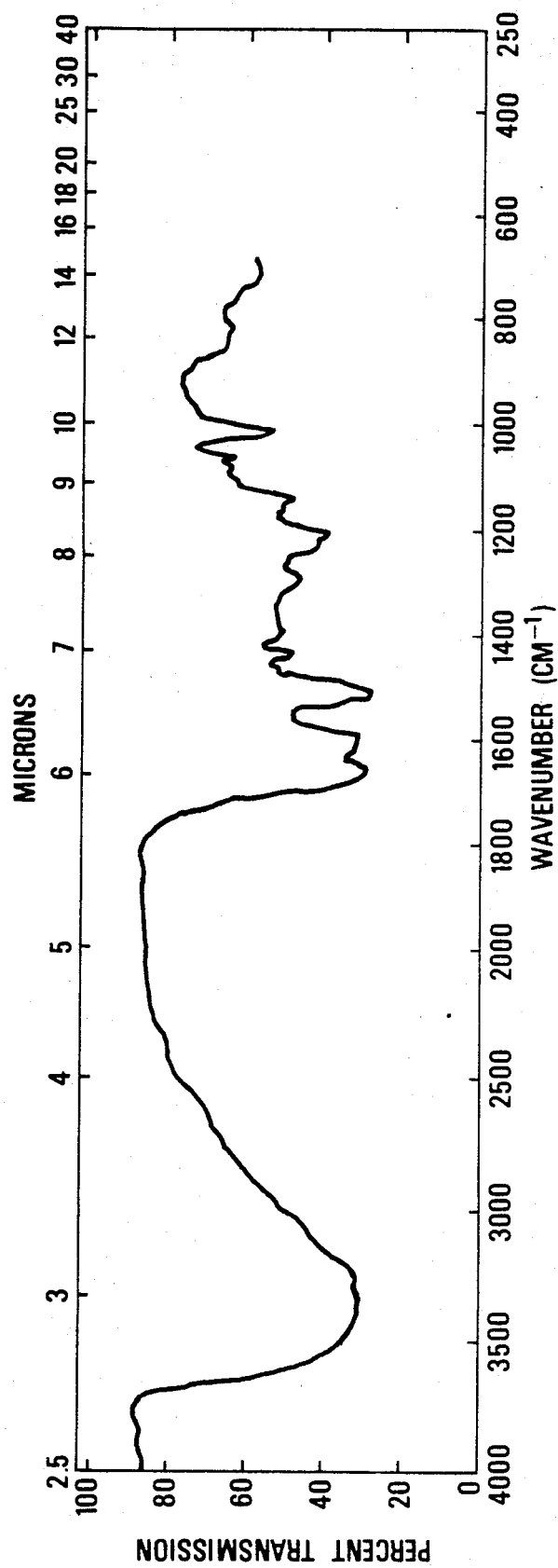

The infrared absorption spectrum of antibiotic A41030 factor E in KBr pellet is shown in the accompanying drawings as FIG. 5. The following distinguishable absorption maxima are observed: 3448–3226 (strong, broad), 1653 (strong), 1600 (medium), 1504 (strong), 1429 (weak), 1290 (weak), 1198 (medium), 1136 (weak), 1064 (weak), and 1010 (strong) cm$^{-1}$.

The ultraviolet absorption maxima of A41030 factor E in neutral, acidic, and basic methanol:water (1:1) are recorded in Table 4.

Antibiotic A41030 factor E is soluble in the same solvents as factor A.

On the basis of the observed physical chemical data, the following structure has been assigned to A41030 factor E.

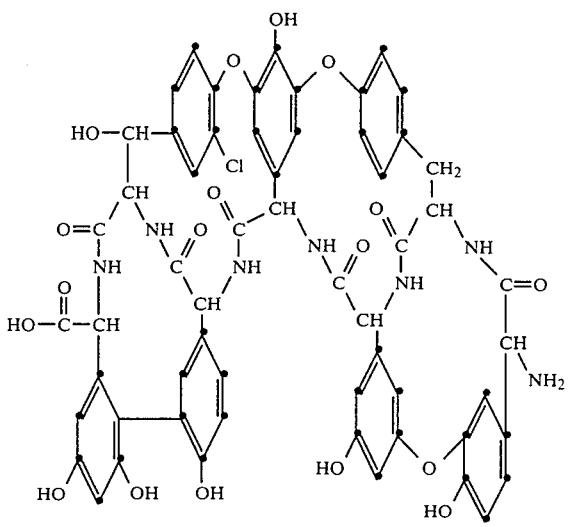

A41030 FACTOR F

Antibiotic A41030 factor F is a white solid having an approximate elemental analysis as follows: 51.39% carbon, 3.96% hydrogen, 6.45% chlorine, 6.45% nitrogen, and 28.65% oxygen. Electrometric titration of factor F in 66% dimethylformamide in water indicated the presence of two titratable groups at $pK_a$ values of about 5.4 and 7.1, respectively, with possibly additional $pK_a$'s >10 (inidial pH 5.93). An observed molecular weight of about 1555 was obtained using fast atom bombardment mass spectrometry. A tentative empirical formula of $C_{70}H_{64}Cl_3N_7O_{28}$ is assigned to factor F.

The molecular weight data suggest that factor F differs from factor A by the addition of a disaccharide substituent comprised of two galactose moieties attached through the phenol group corresponding to the phenol group of factor C to which phenol group a single galactose moiety is attached.

Figure 6:
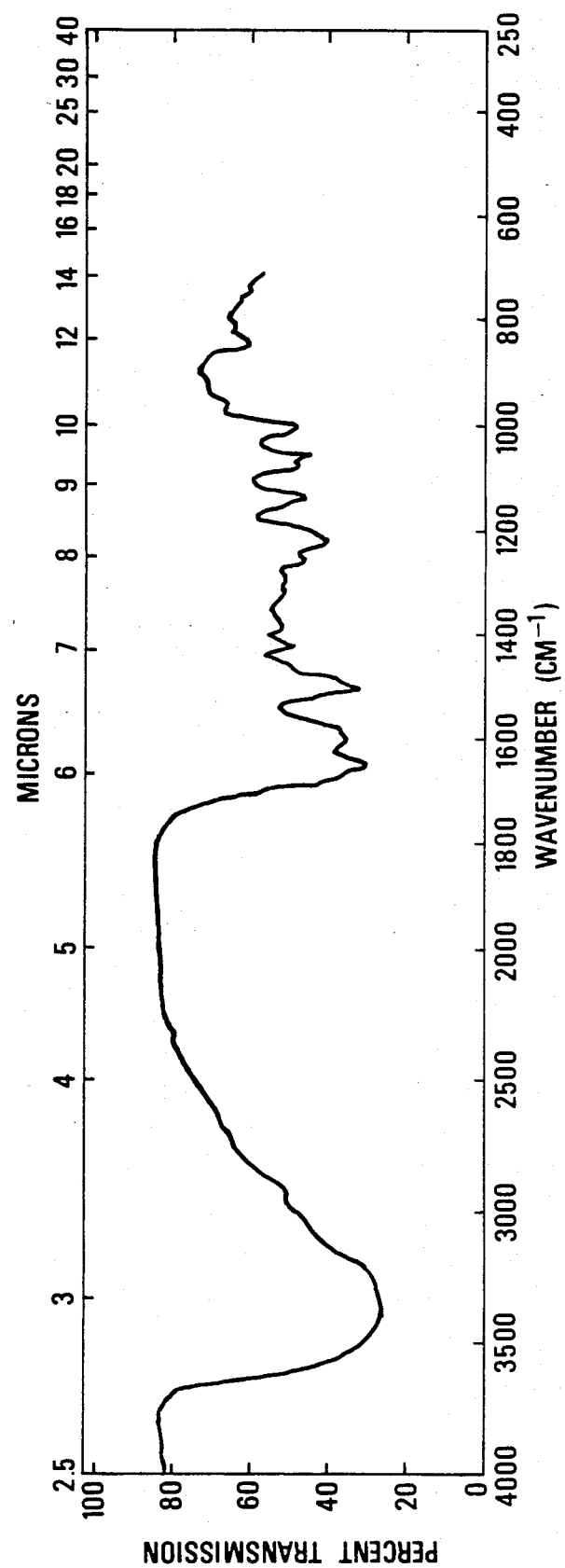

The infrared absorption spectrum of antibiotic A41030 factor F in KBr pellet is shown in the accompanying drawings as FIG. 6. The following distinguishable absorption maxima are observed: 3448–3226 (strong, broad), 1653 (strong), 1600 (medium), 1504 (strong), 1429 (weak), 1258 (weak), 1227 (strong), 1136 (strong), 1075 (strong), 1053 (strong), and 1010 (strong) cm$^{-1}$.

The ultraviolet absorption maxima of A41030 factor F in neutral, acidic, and basic methanol:water (1:1) are recorded in Table 4.

Antibiotic A41030 factor F is soluble in the same solvents as factor A.

A41030 FACTOR G

Antibiotic A41030 factor G is a white solid having an approximate elemental analysis as follows: 50.02% carbon, 4.61% hydrogen, 4.74% chlorine, 6.11% nitrogen, and 30.70% oxygen. Electrometric titration of factor G in 66% dimethylformamide in water indicated the presence of titratable groups at $pK_a$ values of about 5.4 and 7.0, respectively, with possibly additional $pK_a$'s >10.5 (initial pH 6.32). An observed molecular weight of about 1684 was obtained using fast atom bombardment mass spectrometry. Factor G has a disaccharide substituent comprised of two galactose moieties attached through a phenol group in the same manner and in the same location in the molecule as described above for factor F.

Factor G also has two equivalent n-butyl groups attached to the nucleus at an as yet undetermined location. A tentative empirical formula of $C_{78}H_{83}Cl_3N_8O_{28}$ is assigned to factor G.

Figure 7:
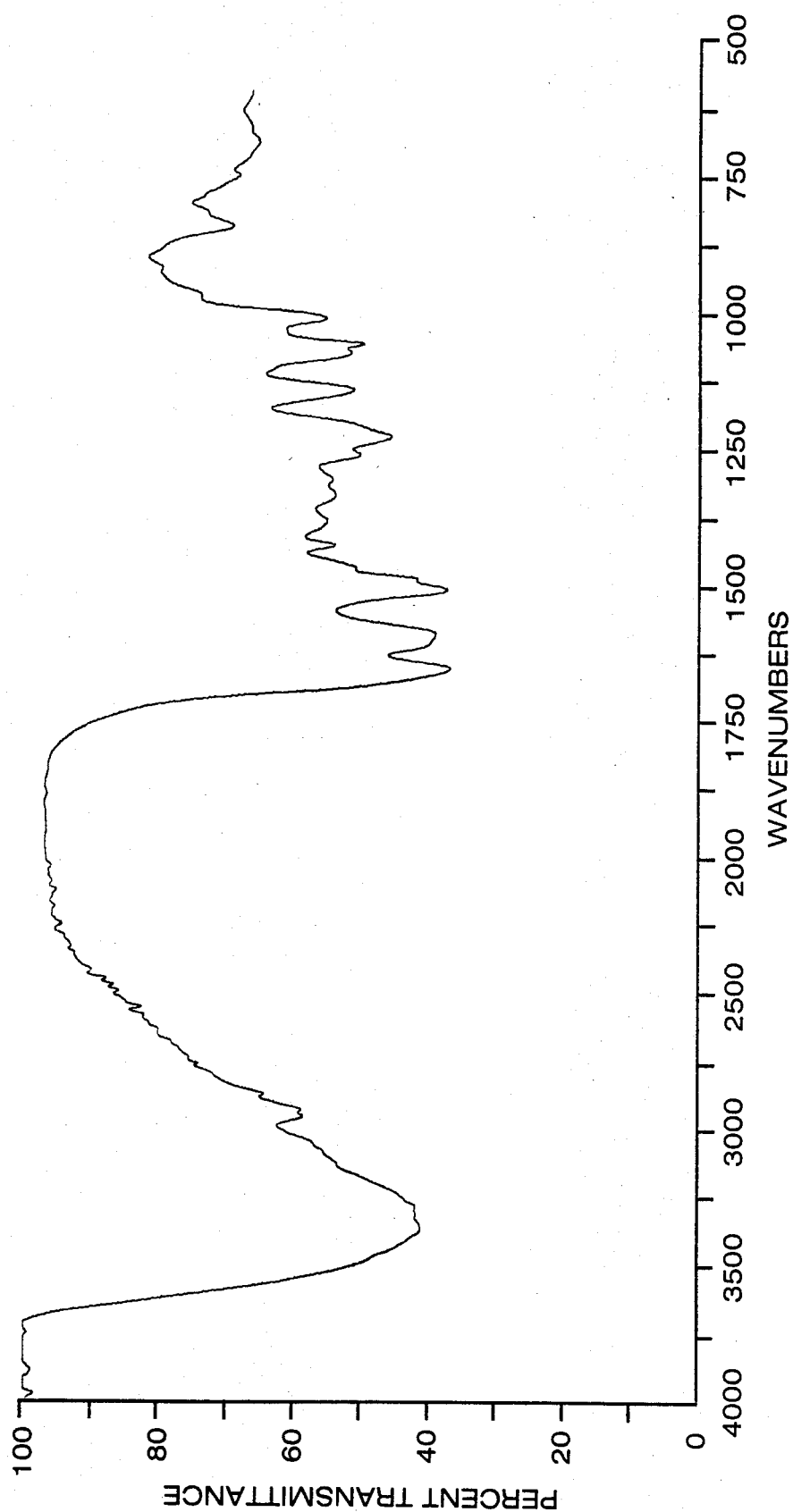

The infrared absorption spectrum of antibiotic A41030 factor G in KBr pellet is shown in the accompanying drawings as FIG. 7. The following distinguishable absorption maxima are observed: 3320 (very broad, strong), 2975 (sharp, weak), 2920 (sharp, weak), 1659 (normal, strong), 1594 (broad, strong), 1512 (sharp, strong), 1492 (shoulder), 1430 (sharp, weak), 1386 (broad, weak), 1337 (broad, weak), 1308 (sharp, weak), 1264 (sharp, weak), 1230 (broad, medium), 1145 (broad, medium), 1077 (sharp, medium), 1062 (sharp, medium), 1014 (sharp, medium), and 846 (broad, medium) cm$^{-1}$.

The ultraviolet absorption maxima of A41030 factor G in neutral, acidic, and basic methanol:water (1:1) are recorded in Table 4.

Antibiotic A41030 factor G is soluble in the same solvents as is factor A.

The ultraviolet absorption characteristics of the A41030 factors are presented in the following Table 4.

TABLE 4

| | UV Spectrophotometry of A41030 Factors | |
|---|---|---|
| Factor | Acidic or Neutral max nm ($\epsilon$) | Basic max nm ($\epsilon$) |
| A | 278 (11,100) | 298 (17,200) |
| B | 278 (9,600) | 298 (16,800) |
| C | 278 (8,400) | 298 (14,000) |
| D | 278 (10,600) | 298 (19,900) |
| E | 278 (8,500) | 298 (15,500) |
| F | 278 (9,300) | 298 (14,500) |
| G | 278 (15,000) | 298 (18,000) |

Factors A, B, C, D, E, F, and G of the A41030 complex can be separated and distinguished from one another by employing silica-gel thin-layer chromatography (TLC) and paper chromatography. *Bacillus subtilis* was the organism used for the bioautography. The ratio of movement (Rx), expressed relative to that of A41030 factor A, which was given a value of 1.00, is set forth in Table 5, which follows.

TABLE 5

| | Rx Solvent System | |
|---|---|---|
| Factor | A | B |
| A | 1.00 | 1.00 |
| B | 0.76 | 0.75 |
| C | 0.68 | 0.44 |
| D | 0.65 | 0.91 |
| E | 0.49 | 0.63 |
| F | 0.21 | 0.25 |
| G | 0.21 | 0.25 |

System A
Paper: Whatman No. 1 (untreated).
Solvent: n-Butanol saturated with water:methanol (1:1).
System B
Sorbent: Merck-Darmstadt-Silica Gel 60.
Solvent: Acetonitrile:ethanol:water (8:1:1.5).

The high performance liquid chromatography (HPLC) retention times of A41030 factors A through G, inclusive, were determined using a stainless steel column having 10 micron LiChrosorb RP-18 as the packing, with a solvent consisting of water:acetonitrile:-dibutylamine (82:18:0.03M) adjusted to pH 2.5 with phosphoric acid. The solvent was applied at a flow rate of 0.75 ml./min. The eluate was monitored by UV absorption at 225 nm. The relative retention values, which are the ratio of the retention time for each factor relative to that of A41030 factor A, are set forth in Table 6, which follows.

TABLE 6

| Factor | Cm. | Min. | Relative Retention |
|---|---|---|---|
| A | 6.4 | 19.2 | 1.00 |
| B | 4.1 | 12.3 | 0.64 |
| C | 5.4 | 16.2 | 0.84 |
| D | 3.8 | 11.4 | 0.59 |
| E | 2.7 | 8.1 | 0.42 |
| F | 4.5 | 13.5 | 0.70 |
| G | 4.5 | 13.5 | 0.70 |

Since the several factors of antibiotic A41030 are amphoteric, containing both an amino group and a carboxylic acid function, they are capable of forming salts with suitable acids and bases. The pharmaceutically acceptable salts so formed are also part of this invention. "Pharmaceutically-acceptable" salts are salts in which the toxicity of the compound as a whole toward warm-blooded animals is not increased relative to the non-salt form. Representative and suitable salts of A41030 factors A, B, C, D, E, F, and G include those acid addition salts formed by standard reaction with both organic and inorganic acids such as, for example, sulfuric, phosphoric, hydrochloric, acetic, succinic, citric, lactic, maleic, fumaric, palmitic, cholic, pamoic, mucic, D-glutamic, d-camphoric, glutaric, glycolic, phthalic, tartaric, lauric, stearic, salicyclic, methanesulfonic, benzenesulfonic, sorbic, picric, benzoic, cinnamic and like acids, as well as salts formed with the carboxylic acid function with such bases as sodium hydroxide, sodium carbonate, potassium carbonate, calcium hydroxide, potassium hydroxide, trimethylamine, ammonium hydroxide, diethanolamine, and like bases.

Antibiotic A41030 complex and factors are active against gram positive microorganisms, including Staphylococcus and Streptococcus species. These antibiotics also show activity for growth promotion and improving feed efficiency in poultry, swine, and cattle.

The in vitro antimicrobial activity of the A41030 complex and the individual factors has been demonstrated by a number of tests which are described hereinafter.

AGAR-DILUTION ASSAY PROCEDURE

The agar-dilution procedure described by the International Collaborative study (ICS) group was used to determine the minimum inhibitory concentrations (MIC's).

The results obtained from tests of antibiotic A41030 factor A in the agar-dilution assay procedure are given in Table 7, which follows.

TABLE 7

| ACTIVITY OF A41030 FACTOR A | |
|---|---|
| Test Organism | MIC ($\mu$g./ml.) |
| Staphylococcus aureus 3055* | <0.5 |
| Staphylococcus aureus 3074** | <0.5 |
| Streptococcus faecalis X66 | <0.5 |

*benzylpenicillin-susceptible
**benzylpenicillin-resistant

DISC-PLATE SENSITIVITY PROCEDURE

Agar plates, inoculated with the test organism, were used; 6 mm. discs (0.02 ml. capacity) were saturated from log 2 dilutions of the antibiotic solution. Disc content was 1/5 or 1/50th of the concentration of the solution used, i.e., disc content of 100 $\mu$g. or 10 $\mu$g. obtained from a solution of 500 $\mu$g./ml. concentration. The size of the zone of inhibition produced by the A41030 factor A antibiotic for each disc content is reported in Table 8, which follows.

TABLE 8

| ACTIVITY OF A41030 FACTOR A | | |
|---|---|---|
| | Zone diameter (mm) (at $\mu$g./disc) | |
| Test Organism | 100 | 10 |
| Staphylococcus aureus 3055* | 20.8 | 17.2 |
| Staphylococcus aureus 3074** | 19.8 | 16.7 |
| Staphylococcus aureus 3130*** | 21.4 | 17.4 |
| Streptococcus pyogenes C203 | 15.0 | 12.0 |
| Streptococcus sp. (Group D) 9960 | 20.5 | 16.4 |
| Streptococcus pneumoniae Park I | 17.0 | 15.0 |
| Escherichia coli EC14 | 8.0 | 0 |

*benzylpenicillin-suseptible
**benzylpenicillin-resistant
***benzylpenicillin-resistant, methicillin-resistant Antibiotic A41030 factor A has shown activity against a number of strains of Hemophilus influenzae, as determined by the agar-dilution method. The results of the tests are recorded in Table 9, which follows.

TABLE 9

| ACTIVITY OF A41030 FACTOR A AGAINST HEMOPHILUS INFLUENZAE STRAINS | |
|---|---|
| Hemophilus influenzae | MIC ($\mu$g./ml.) |
| R251 | 16 |
| R259 | 16 |
| R272 | 16 |
| R274 | 16 |
| 4842 | 8 |
| 75-90383 | 16 |
| P. Wylie | 16 |
| G. Newton | 32 |
| Bruno | 16 |
| 75-19300 | 16 |
| S. Ford | 16 |
| A. Hall | 16 |
| C. Steele | 16 |
| Miller | 16 |
| Howard | 16 |
| 75-312 | 8 |
| 75-313 | 16 |
| 75-364 | 16 |
| 75-465 | 32 |

Antibiotic A41030 factor A is active against Neisseria sp., as determined by the agar-dilution method. The test results are recorded in Table 10, which follows.

TABLE 10

| ACTIVITY OF A41030 FACTOR A AGAINST NEISSERIA SP. | |
|---|---|
| Neisseria sp. | MIC ($\mu$g./ml.) |
| L. Nance | 4.0 |
| Woods | 4.0 |
| Schultz | 8.0 |
| Mitchell | 4.0 |
| Sanders | 1.0 |

The activity of antibiotic A41030 factor A against a variety of bacteria, as determined by the agar-dilution method, is reported in Table 11, which follows.

TABLE 11

ACTIVITY OF A41030 FACTOR A AGAINST A VARIETY OF BACTERIA

| Bacteria | MIC (µg./ml.) |
|---|---|
| Staphylococcus aureus | |
| 3055[1] | 0.13 |
| 3074* | ≦0.06 |
| 3131** | ≦0.06 |
| 3134** | ≦0.06 |
| H43* | ≦0.06 |
| V57* | ≦0.06 |
| H290 | ≦0.06 |
| Streptococcus pyogenes | |
| C203 | 0.25 |
| 9943 | 0.25 |
| 10389 | 0.25 |
| 12344 | 0.5 |
| M-6517 | 0.25 |
| Streptococcus pneumoniae | |
| Park I | 0.25 |
| Type 14 | 0.25 |
| 2764 | 0.25 |
| 6301 | 0.25 |
| BI-343 | 0.25 |
| Staphylococcus epidermidis | |
| Litton | 0.13 |
| Mencher | ≦0.06 |
| Britton | 0.13 |
| Mobley | ≦0.06 |
| Viridans streptococcus | |
| SM-1134 | 0.5 |
| SSI-910 | 0.25 |
| SSII-895 | 0.25 |
| Streptococcus sp. (Group D) | |
| 238 | 0.25 |
| 282 | 0.25 |
| 9901 | 0.25 |
| 12253F | 0.25 |
| Guze | 0.25 |
| Shigella flexneri | |
| SH-3 | 128 |
| SH-4 | 64 |

*Penicillin-resistant
**Penicillin, methicillin, and erythromycin resistant
[1]The name or number under the named organism is the strain designation.

The A41030 antibiotics, factors A, B, and C, are active against a genus of anaerobic bacteria identified as Bacteroides sp., the 24-hour MIC values being determined by the agar-dilution method, and are set forth in Table 12, which follows.

TABLE 12

ACTIVITY OF A41030 FACTORS AGAINST BACTEROIDES SP.

| Test Organism | MIC (µg./ml.) | | |
|---|---|---|---|
| | A | B | C |
| B. fragilis 1877 | 32 | 32 | 32 |
| B. fragilis 103 | 32 | 32 | 32 |
| B. fragilis 104 | 32 | 32 | 32 |
| B. fragilis 106 | 64 | 32 | 32 |
| B. fragilis 107 | 32 | 32 | 32 |
| B. fragilis 108 | 32 | 32 | 64 |
| B. fragilis 110 | 64 | 64 | 64 |
| B. fragilis 111 | 32 | 32 | 32 |
| B. fragilis 112 | 64 | 32 | 32 |
| B. fragilis 113 | 32 | 32 | 32 |
| B. fragilis 1451 | 64 | 64 | 64 |
| B. fragilis 1470 | 64 | 64 | 64 |
| B. fragilis 2 | 64 | 32 | 32 |
| B. fragilis 9 | 64 | 32 | 32 |
| B. fragilis 9032 | 64 | 32 | 32 |
| B. corrodens 1874 | 32 | 32 | 32 |
| B. vulgatis 1563 | 32 | 32 | 32 |
| B. thetaiotaomicron 1438 | 64 | 32 | 32 |
| B. thetaiotaomicron 1900A | 128 | 128 | 128 |

Antibiotic A41030 factors A, B and C have also been tested and found to be active against a genus of anaerobic bacteria identified as Propionibacterium acnes. The MIC values were determined by the 24-hour agar-dilution method, and are set forth in Table 13, which follows.

TABLE 13

ACTIVITY OF A41030 FACTORS AGAINST PROPIONIBACTERIUM ACNES

| Strain of | MIC (µg./ml.) | | |
|---|---|---|---|
| P. acnes | A | B | C |
| 44 | 0.125 | 0.06 | 0.125 |
| 79 | 0.125 | 0.06 | 0.125 |
| 101 | 0.125 | 0.06 | 0.125 |
| 103 | 0.125 | 0.06 | 0.125 |
| 104 | 0.25 | 0.25 | 0.25 |
| 105 | 0.125 | 0.06 | 0.125 |
| 106 | 0.125 | 0.06 | 0.125 |
| 107 | 0.06 | 0.06 | 0.125 |
| 5292 | 0.06 | 0.06 | 0.06 |
| 5170 | ≦0.03 | ≦0.03 | ≦0.03 |
| 5176 | ≦0.03 | 0.06 | ≦0.03 |
| 5187 | ≦0.03 | 0.06 | 0.06 |
| 5191 | 0.125 | 0.06 | 0.125 |
| 5197 | ≦0.03 | 0.06 | ≦0.03 |
| 5226 | 0.5 | 0.5 | 0.125 |
| 5227 | ≦0.03 | 0.06 | 0.06 |
| 5228 | 1.0 | 0.5 | 1.0 |
| 5229 | 0.5 | 0.25 | 0.5 |
| 5246 | 0.06 | 0.125 | 0.06 |

Antibiotic A41030 factors A, B, C, D, E, F, and G have been tested and found to be active against a number of anaerobic bacteria, as recorded in Table 14, which follows, the MIC values having been determined by the agar-dilution method.

TABLE 14

ACTIVITY OF A41030 FACTORS AGAINST ANAEROBIC BACTERIA

| Test Organism | MIC (µg./ml.) | | | | | | |
|---|---|---|---|---|---|---|---|
| | A | B | C | D | E | F | G |
| Clostridium difficile 2994 | 32 | 32 | 16 | 0.5 | 0.5 | 1.0 | 2 |
| Clostridium perfringens 81 | 0.5 | 0.5 | 1.0 | 0.5 | 1.0 | 1.0 | 2 |
| Clostridium septricum 1128 | 2 | 4 | 8 | 0.25 | 0.5 | 1.0 | 2 |
| Eubacterium aerofaciens 1235 | >128 | >128 | >128 | 0.5 | 0.5 | 1.0 | 2 |
| Peptococcus asaccharolyticus 1302 | ≦0.125 | ≦0.25 | ≦0.25 | ≦0.125 | ≦0.25 | ≦0.25 | 1.0 |
| Peptococcus prevoti 1281 | ≦0.25 | ≦0.25 | ≦0.25 | 0.25 | 32 | 32 | 2 |
| Peptostreptococcus anaerobius 1428 | ≦0.25 | ≦0.25 | ≦0.25 | 0.5 | 32 | 32 | ≦0.5 |
| Peptostreptococcus intermedius 1264 | 1.0 | 0.5 | 0.5 | 1.0 | 32 | 1.0 | 2 |
| Propionibacterium acnes 79 | ≦0.25 | 16 | ≦0.25 | 0.25 | 0.5 | 1.0 | 1.0 |
| Bacteroides fragilis 111 | 128 | 64 | >128 | 32 | 64 | 32 | 32 |

TABLE 14-continued

ACTIVITY OF A41030 FACTORS AGAINST ANAEROBIC BACTERIA

| Test Organism | MIC (μg./ml.) | | | | | | |
|---|---|---|---|---|---|---|---|
| | A | B | C | D | E | F | G |
| *Bacteroides fragilis* 1877 | 32 | 32 | 16 | 32 | 32 | 32 | 32 |
| *Bacteroides fragilis* 1936B | 64 | 32 | 32 | 32 | 64 | 32 | 64 |
| *Bacteroides thetaiotaomicron* 1438 | 64 | 32 | 64 | 32 | 64 | 64 | 64 |
| *Bacteroides melaninogenicus* 1856/28 | >128 | >128 | >128 | >64 | >128 | >128 | >128 |
| *Bacteroides melaninogenicus* 2736 | 4 | 4 | 4 | 0.5 | 32 | 1.0 | 64 |
| *Bacteroides vulgatis* 1211 | 32 | 32 | 32 | 32 | 32 | 32 | 64 |
| *Bacteroides corrodens* 1874 | 64 | 64 | 32 | 32 | 64 | 32 | 32 |
| *Fusobacterium symbiosum* 1470 | 1.0 | 1.0 | 1.0 | 0.5 | 1.0 | 1.0 | 2 |
| *Fusobacterium necrophorum* 6054A | 8 | 8 | 16 | ≦0.125 | 0.5 | 1.0 | 2 |

Antibiotic A41030 factors A, B, and C have shown activity against a number of species of two genera of anaerobic cocci identified as Peptococcus and Peptostreptococcus, respectively. The MIC values were determined by the agar-dilution method, and are recorded in Table 15, which follows.

TABLE 15

ACTIVITY OF A41030 FACTORS vs. *PEPTOCCUS* AND *PEPTOSTREPTOCOCCUS* SPECIES

| Test Organism | MIC (μg./ml.) | | |
|---|---|---|---|
| | A | B | C |
| *Pc.*[1] *asaccharolyticus* 1302 | ≦0.03 | 0.125 | 0.125 |
| *Pc. asaccharolyticus* 1344 | 0.5 | 0.5 | 1.0 |
| *Pc. constellatus* 1468 | 0.5 | 0.5 | 0.5 |
| *Pc. magnus* 1401 | 0.125 | 0.125 | 0.25 |
| *Pc. magnus* 1421 | 0.125 | 0.125 | 0.25 |
| *Pc. magnus* 1477 | 0.5 | 0.25 | 0.5 |
| *Pc. prevoti* 1281 | 0.5 | 0.5 | 1.0 |
| *Pc. prevoti* 1293 | 1.0 | 0.25 | 0.5 |
| *Pc. prevoti* 1407 | 1.0 | 0.5 | 1.0 |
| *Ps.*[2] *anaerobius* 8 | 0.5 | 0.25 | 0.5 |
| *Ps. anaerobius* 52 | 0.5 | 0.5 | 0.25 |
| *Ps. anaerobius* 59 | 0.5 | 0.25 | 0.25 |
| *Ps. anaerobius* 1418 | ≦0.03 | 0.06 | ≦0.03 |
| *Ps. anaerobius* 1451 | 0.5 | 0.25 | 0.25 |
| *Ps. anaerobius* 1428 | 0.5 | 0.25 | 0.25 |
| *Ps. anaerobius* 1477 | 0.5 | 0.125 | 0.25 |
| *Ps. intermedius* 1264 | ≦0.03 | ≦0.03 | ≦0.03 |
| *Ps. intermedius* 1524 | 0.5 | 0.25 | 0.5 |
| *Ps. intermedius* 1624 | 1.0 | 0.5 | 1.0 |

[1]Pc = Peptococcus
[2]Ps = Peptostreptococcus

The A41030 antibiotic factors A, B, C, D, E, F, and G, are also active against a number of strains of *Clostridium difficile*, as determined by the agar-dilution method. The results of the tests are recorded in Table 16, which follows.

TABLE 16

ACTIVITY OF A41030 FACTORS AGAINST *CLOSTRIDIUM DIFFICILE* STRAINS

| Clostridium difficile | MIC (μg./ml.) | | | | | | |
|---|---|---|---|---|---|---|---|
| | A | B | C | D | E | F | G |
| 8484 | 1.0 | 1.0 | 1.0 | ≦0.25 | 0.5 | 1.0 | 1.0 |
| 6890 | 1.0 | 1.0 | 2 | 0.5 | 0.5 | 1.0 | 1.0 |
| 2634 | 1.0 | 1.0 | 2 | 0.5 | 1.0 | 2 | 1.0 |
| 78 | 1.0 | 0.5 | 1.0 | ≦0.25 | 0.5 | 1.0 | 1.0 |
| A-194 | 1.0 | 1.0 | 2 | ≦0.25 | 0.5 | 1.0 | 1.0 |
| A-195 | 1.0 | 1.0 | 1.0 | ≦0.25 | 0.5 | 1.0 | 1.0 |
| A-196 | 1.0 | 1.0 | 2 | 0.5 | 1.0 | 2 | 1.0 |
| A-279 | 1.0 | 1.0 | 2 | ≦0.25 | 0.5 | 1.0 | 1.0 |
| A-280 | 1.0 | 0.5 | 1.0 | ≦0.25 | 0.5 | 1.0 | 1.0 |
| A-281 | 1.0 | 1.0 | 2 | 0.5 | 1.0 | 2 | 1.0 |
| WAL-2112 | 1.0 | 1.0 | 2 | ≦0.25 | 0.5 | 1.0 | 1.0 |
| WAL-3657 | 1.0 | 1.0 | 2 | ≦0.25 | 0.5 | 1.0 | 1.0 |
| WAL-4268 | 1.0 | 0.5 | 1.0 | ≦0.25 | 0.5 | 1.0 | 1.0 |
| 107B | 1.0 | 0.5 | 1.0 | ≦0.25 | 0.5 | 1.0 | 1.0 |
| 111F | 1.0 | 1.0 | 2 | ≦0.25 | 0.5 | 2 | 1.0 |
| 1153 | 1.0 | 1.0 | 2 | 1.0 | 1.0 | 2 | 1.0 |
| 3424-5B | 1.0 | 1.0 | 1.0 | 0.5 | 0.5 | 1.0 | 1.0 |
| 3816 | 1.0 | 1.0 | 2 | 0.5 | 0.5 | 1.0 | 1.0 |
| 3950D | 1.0 | 1.0 | 2 | 0.5 | 0.5 | 1.0 | 1.0 |

The in vitro activity of antibiotic A41030 factors A, B, C, D, E, F, and G against a number of aerobic bacteria has been determined using a standard agar-dilution assay. The results after reading the end point after 24 hours are recorded in Table 17, which follows.

TABLE 17

ACTIVITY OF A41030 FACTORS AGAINST AEROBIC BACTERIA

| Test Organism | MIC (μg./ml.) | | | | | | |
|---|---|---|---|---|---|---|---|
| | A | B | C | D | E | F | G |
| *Staphylococcus aureus* 3055 | 0.125 | 0.125 | 0.5 | 0.25 | 0.125 | 0.5 | 0.5 |
| *Staphylococcus aureus* V41 | 0.125 | 0.125 | 0.5 | 0.25 | 0.25 | 0.5 | 1 |
| *Staphylococcus aureus* X400 | 0.5 | 0.25 | 1 | 0.25 | 0.25 | 1 | 2 |
| *Staphylococcus aureus* S13E | 0.25 | 0.125 | 0.5 | 0.25 | 0.25 | 1 | 1 |
| *Staphylococcus epidermidis* EPI1 | 0.125 | 0.125 | 0.5 | 0.25 | 0.25 | 0.25 | 0.5 |
| *Staphylococcus epidermidis* EPI2 | 1 | 0.5 | 2 | 1 | 2 | 2 | 0.5 |
| *Streptococcus pyogenes* C203 | 0.5 | 0.25 | 1 | 0.5 | 0.25 | 2 | 2 |
| *Streptococcus pneumoniae* Park I | 0.5 | 0.5 | 1 | 0.5 | 0.25 | 2 | 2 |
| Streptococcus sp. Group D X66 | 1 | 1 | 2 | 1 | 1 | 4 | 4 |
| Streptococcus sp. Group D 9960 | 2 | 1 | 4 | 1 | 1 | 4 | 4 |
| *Haemophilus influenzae* Brun | 8 | 8 | 16 | — | — | — | — |
| *Haemophilus influenzae* 251 | 2 | 2 | 4 | — | — | — | — |
| *Haemophilus influenzae* C.L. | — | — | — | 8 | 8 | 32 | 32 |
| *Haemophilus influenzae* 76 | — | — | — | 8 | 8 | 32 | 32 |
| *Shigella sonnei* N9 | >128 | 128 | >128 | >128 | >128 | >128 | >128 |
| *Escherichia coli* N10 | >128 | 128 | >128 | >128 | >128 | >128 | >128 |
| *Escherichia coli* EC14 | 128 | 128 | >128 | >128 | >128 | >128 | >128 |
| *Escherichia coli* TEM | >128 | 128 | >128 | 64 | >128 | >128 | >128 |
| *Klebsiella pneumoniae* X26 | >128 | >128 | >128 | 128 | >128 | >128 | 64 |
| *Klebsiella pneumoniae* KAE | >128 | >128 | >128 | >128 | >128 | >128 | >128 |
| *Klebsiella pneumoniae* X68 | >128 | 128 | >128 | >128 | >128 | >128 | >128 |

TABLE 17-continued

ACTIVITY OF A41030 FACTORS AGAINST AEROBIC BACTERIA

| Test Organism | MIC (μg./ml.) | | | | | | |
|---|---|---|---|---|---|---|---|
| | A | B | C | D | E | F | G |
| Enterobacter aerogenes C32 | >128 | 64 | >128 | >128 | >128 | >128 | >128 |
| Enterobacter aerogenes EB17 | >128 | >128 | >128 | >128 | >128 | >128 | >128 |
| Enterobacter cloacae EB5 | >128 | 128 | >128 | >128 | >128 | >128 | >128 |
| Enterobacter cloacae 265A | >128 | 128 | >128 | >128 | >128 | >128 | >128 |
| Salmonella typhi X514 | >128 | >128 | >128 | >128 | >128 | >128 | >128 |
| Salmonella typhi 1335 | >128 | >128 | >128 | >128 | >128 | >128 | >128 |
| Pseudomonas aeruginosa X528 | >128 | >128 | >128 | >128 | >128 | >128 | >128 |
| Pseudomonas aeruginosa X239 | >128 | >128 | >128 | >128 | >128 | >128 | >128 |
| Pseudomonas aeruginosa Ps18 | >128 | >128 | >128 | >128 | >128 | >128 | >128 |
| Pseudomonas aeruginosa Ps72 | — | — | — | >128 | >128 | >128 | >128 |
| Serratia marcescens X99 | >128 | 128 | >128 | >128 | >128 | >128 | >128 |
| Serratia marcescens SE3 | >128 | >128 | >128 | >128 | >128 | >128 | >128 |
| Proteus morganii PR15 | >128 | >128 | >128 | >128 | >128 | >128 | >128 |
| Proteus inconstans PR33 | >128 | >128 | >128 | >128 | >128 | >128 | >128 |
| Proteus rettgeri PR7 | >128 | >128 | >128 | — | — | — | — |
| Proteus rettgeri C24 | >128 | >128 | >128 | >128 | >128 | >128 | >128 |
| Citrobacter freundii CF17 | >128 | 128 | >128 | >128 | >128 | >128 | >128 |
| Bordetella bronchiseptica 16 | >128 | >128 | >128 | — | — | — | — |
| Acinetobacter calcoaceticus AC12 | — | — | — | >128 | >128 | >128 | >128 |

— = not tested

The in vitro activity of antibiotic A41030 factors A and B against a number of representative aerobic, gram-positive bacteria, including Streptococcus sp. Group D, has been determined using a standard agar-dilution assay. The results, determined by reading the end point after 24 hours, are recorded in Table 18, which follows.

TABLE 18

ACTIVITY OF A41030 FACTORS A AND B AGAINST AEROBIC BACTERIA

| Test Organism | MIC (μg./ml.) | |
|---|---|---|
| | A | B |
| Staphylococcus aureus | | |
| 3055 | 0.06 | 0.06 |
| X400 | 0.125 | 0.125 |
| V138 | 0.06 | 0.06 |
| V140 | 0.125 | 0.125 |
| V102 | 0.125 | 0.125 |
| Staphylococcus epidermidis | | |
| 222 | 0.125 | 0.125 |
| 270 | 0.06 | 0.06 |
| 285 | 0.06 | 0.03 |
| 219 | 0.06 | 0.03 |
| 269 | 0.06 | 0.03 |
| Streptococcus pyogenes C203 | 0.25 | 0.125 |
| Streptococcus sp. ATCC 10389 | 0.125 | 0.25 |
| Streptococcus sp. Group B | | |
| 5 | 1 | 1 |
| 14 | 0.06 | 0.125 |
| Streptococcus sp. Group D | | |
| X66 | 0.25 | 0.25 |
| 9960 | 0.5 | 0.5 |
| 2041 | 0.5 | 0.5 |
| 8043 | 0.25 | 0.25 |
| 9901 | 1 | 1 |
| 12253F | 0.25 | 0.5 |
| Mx161 | 0.25 | 0.25 |
| 2058 | 0.5 | 0.5 |
| Streptococcus pneumoniae Park I | 0.125 | 0.125 |
| Streptococcus pneumoniae B1-438 | 0.25 | 0.5 |
| Haemophilus parainfluenzae 7901 | 16 | 16 |
| Haemophilus parainfluenzae 9796 | 16 | 16 |
| Haemophilus influenzae | | |
| C.L. | 4 | 8 |
| Mx366 | 2 | 4 |
| Mx371 | 2 | 4 |
| 76 | 4 | 4 |
| Bond | 2 | 4 |
| 16836 | 4 | 4 |
| 4842 | 2 | 4 |
| 312 | 2 | 4 |

The activity of antibiotic A41030 complex against a number of animal pathogens was determined by a standard in vitro antimicrobial broth microtiter test, and the results are set forth in Table 19, which follows.

TABLE 19

ACTIVITY OF A41030 COMPLEX AGAINST SEVERAL ANIMAL PATHOGENS

| Test Organism | MIC (μg./ml.) |
|---|---|
| Staphylococcus sp. 1130 | <0.78 |
| Streptococcus sp. 80 | <0.78 |
| Pasteurella multocida (bovine) | 3.12 |
| Pasteurella hemolytica | 6.25 |
| Bordetella bronchiseptica (Switzer) | 50.00 |
| Escherichia coli | 50.00 |
| Mycoplasma synoviae | 50.00 |
| Mycoplasma hyorhinis | 50.00 |
| Pseudomonas-fish | <0.78 |
| Aeromonas liquefaciens | 50.00 |

All of the A41030 factors tested have shown in vivo antimicrobial activity against experimental bacterial infections. When two doses of test compound were administered subcutaneously to mice in illustrative infections, the activity observed is measured as an $ED_{50}$ value [effective dose in mg./kg. to protect fifty percent of the test animals: See Warren Wick, et al., J. Bacteriol. 81, 233-235 (1961)]. The $ED_{50}$ values observed for A41030 factors A, B, C, D, E, and F are given in Table 20, which follows.

TABLE 20

| Antibiotic | Staph. aureus $ED_{50}$ | S. pyogenes $ED_{50}$ | S. pneumoniae $ED_{50}$ |
|---|---|---|---|
| A41030A | 1.4 | 2.8 | 1.68 |
| A41030B | <0.43 | 1.4 | 1.4 |
| A41030C | <0.43 | 10.4 | 6.7 |
| A41030D | 0.339 | 3.24 | 2.21 |

TABLE 20-continued

| Antibiotic | Staph. aureus $ED_{50}$ | S. pyogenes $ED_{50}$ | S. pneumoniae $ED_{50}$ |
|---|---|---|---|
| A41030E | <0.31 | 3.54 | 3.11 |
| A41030F | <0.31 | >5.0 | >5.0 |

The acute toxicity of each of the antibiotic A41030 factors A, B, and C, has been determined in mice and has been found to be >300 mg./kg., administered intraperitoneally.

The $LD_{50}$ of each of the antibiotic A41030 factors A, B, and C, has been determined in mice as being >300 mg./kg., when administered intraperitoneally.

The in vivo oral activity of each of the antibiotic A41030 factors A, B, and C, as determined against *S. pyogenes* in mice, is >300 mg./kg. X 2.

In one of its aspects this invention provides a method for treating infections in man or animals which comprises administering to said man or animal a non-toxic antibiotic-effective dose of between about 25 mg. and about 2,000 mg. of an A41030 antibiotic factor, or the A-41030 complex, or a pharmaceutically-acceptable, non-toxic salt of said factor or complex.

Factor A, or a pharmaceutically-acceptable, non-toxic salt thereof, is preferably used in the treatment of infections in man, while in general the complex of factors or a salt thereof is suitable for use in the treatment of infections in animals.

In the treatment of infections in man the antibiotic factor, preferably factor A, is administered by the parenteral route, e.g., by i.m. injection, or i.v. infusion. For injection, the antibiotic or a pharmaceutically-acceptable salt thereof is dissolved in a physiologically-acceptable diluent at the desired concentration and administered. Suitable diluents include for example, Water-for-Injection, 0.9% saline, 5% dextrose, Ringer's solution, or other commonly employed diluent. For administration by i.v. infusion, the antibiotic or salt thereof can be made up in a physiological fluid or dilute nutrient at a suitable concentration; for example, at a concentration between about 5% and about 10%, and slowly infused with the fluid. Alternatively, the antibiotic may be administered by the "piggy-back" method.

The individual factors, combinations of the factors, or the whole complex of factors and the pharmaceutically-acceptable, non-toxic salts thereof can be made up in dosage unit formulations in hermetically sealed vials, sterile, rubber-stoppered vials, or in plastic pouches. Such unit dosage forms can contain excipients such as antioxidants, solubilizing agents, dispersing agents, buffers, and the like. One such dosage unit formulation comprises 100 mg. of factor A, or a pharmaceutically-acceptable salt thereof, in a rubber (butyl rubber) stoppered vial. Another dosage unit formulation comprises 250 mg. of factor A, or a salt thereof, in a sterile, sealed vial. For i.v. infusion a dosage unit formulation of this invention comprises 5 g. of factor A, or a pharmaceutically-acceptable salt thereof, in a plastic pouch.

When A41030 complex or an A41030 factor is used as an antibacterial agent, it may be administered either orally or parenterally. As will be appreciated by those skilled in the art, the A41030 complex or factor is commonly administered together with a pharmaceutically-acceptable carrier or diluent. The dosage of A41030 complex or factor will depend upon a variety of considerations, such as, for example, the nature and severity of the particular infection to be treated. Those skilled in the art will recognize that appropriate dosage ranges and/or dosage units for administration may be determined by considering the MIC and $ED_{50}$ values and toxicity data herein provided, together with factors such as the patient or host and the infecting organism.

The A41030 antibiotics are useful inter alia for suppressing the growth of Staphylococcus, Streptococcus and *Propionibacterium acnes* organisms, and the antibiotics could therefore be used, for example, in the treatment of acne. The A41030 individual factors, or mixtures thereof in the purified state, can be formulated in pharmaceutically-acceptable diluents such as isopropyl alcohol for application to the skin. Such solutions can be made up with antibiotic concentrations of from about 1 to about 15 percent weight per volume. Alternatively, the antibiotics can be made up into creams or lotions for application to the skin.

The A41030 antibiotics are also useful for suppressing the growth of *Clostridium difficile* organisms, which cause Pseudomembranous colitis in the intestine. The A41030 individual factors or mixtures thereof could be used in the treatment of pseudomembranous colitis by the oral administration of a therapeutically-effective dose of said antibiotics or a pharmaceutically-acceptable, non-toxic salt thereof, prepared in a pharmaceutically-acceptable dosage form. For such use the antibiotic can be administered in gelatin capsules or in liquid suspension.

The antibiotics of this invention also can be used in veterinary medicine in the treatment of infectious diseases in domestic and farm animals. They are useful also in animal husbandry, e.g., in enhancing the growth of beef cattle and other ruminants. An especially valuable use for the antibiotics of this invention resides in their ability to increase the production of milk in dairy cattle.

The A41030 complex has shown activity against infectious canine hepatitis virus in vitro at 40 mcg./ml. The A41030 complex has also shown activity in vitro against pseudorabies at 20 mcg./ml; and A41030 factor A has shown activity in vitro against pseudorabies at 20 mcg./ml.

Antibiotic A41030 complex has shown activity as a growth promoter in chickens, the test being carried out as follows:

Chicks, 8-day old Penobscot broilers, were utilized in this test. A total of 560 chicks were used, divided in groups of 7 birds each. There were 35 groups acting as controls, and 5 groups were treated with the antibiotic added to the standard chick ration at the rate of 20 g. of antibiotic A41030 complex per ton of feed. Feed and water were available to all groups ad libitum for 21 days. Two time replicates were run. The criteria for activity: 3% increase in weight gain and/or 2% improvement in feed efficiency in one or both time replicates. The results are set forth in Table 21, which follows.

TABLE 21

| Treatment | Conc. g./T. | Weight Gain gm. | Weight Gain % Impr. | Feed Efficiency F/G | Feed Efficiency % Impr. |
|---|---|---|---|---|---|
| Control | — | 433 | — | 1.671 | — |
| A41030 | 20 | 451 | 4.16 | 1.601 | 4.19 |
| Control | — | 451 | — | 1.673 | — |
| A41030 | 20 | 464 | 2.88 | 1.651 | 1.32 |

F/G = Total feed consumed divided by total weight gain.

Accordingly, this invention provides a method of enhancing the growth of chickens which comprises administering to the chickens in their diet between about 20 and about 30 g. of an A41030 antibiotic factor or the A41030 antibiotic complex, or a pharmaceutically-acceptable salt thereof, per ton of feed. Alternatively, the antibiotic factors or the complex, in the form of a pharmaceutically-acceptable, non-toxic salt can be administered in the drinking water of the chickens.

Antibiotic A41030 also acts as a growth promoter when administered to weanling pigs. The antibiotic was tested in young pigs at several dosage levels, as hereinafter described.

The antibiotic A41030 complex was tested at levels of 5, 20, 50 and 100 ppm. in the diet of pigs initially weighing about 21 pounds (5–7 weeks of age). The experiment was conducted in an environmentally controlled nursery facility. There were five replicates per treatment and five pigs per replicate for the 27-day experiment. The results appear in Table 22, which follows:

TABLE 22

| Treatment | Level ppm | ADG lbs. | % Increase | ADF lbs. | % Increase | F/G | % Improvement |
|---|---|---|---|---|---|---|---|
| Basal | — | 0.67 | — | 1.25 | — | 1.87 | — |
| A41030 | 5 | 0.70 | +4.5 | 1.33 | 6.4 | 1.89 | −1.0 |
| A41030 | 20 | 0.67 | 0.0 | 1.25 | 0.0 | 1.93 | −3.2 |
| A41030 | 50 | 0.71 | +6.0 | 1.25 | 0.0 | 1.78 | 4.8 |
| A41030 | 100 | 0.77 | +14.9 | 1.34 | 7.2 | 1.74 | 7.4 |

ADG = average daily gain
ADF = average daily feed consumption
F/G = ratio of feed consumption to gain In this trial the antibiotic elicited a dose-related improvement in growth performance in weanling pigs, as indicated by the response at 50 ppm and at 100 ppm.

The antibiotic A41030 complex was further tested in weanling pigs (17 pounds, 4–6 weeks of age) at levels of 25, 50 and 100 gm./ton of feed for 35 days. There were four replicates of six pigs per treatment.

Antibiotic A41030 complex when administered to these weanling pigs at the rates taught, increased the rate of gain by 5.6 percent, 8.5 percent, and 7.0 percent; and improved the feed conversion efficiency by 6.6 percent, 9.2 percent, and 3.1 percent, when added to the diet at 25, 50 and 100 gm./ton, respectively. These results are recorded in Table 23, which follows.

TABLE 23

| Treatment | Level gm./ton | ADG lbs. | % Increase | ADF lbs. | % Increase | F/G | % Improvement |
|---|---|---|---|---|---|---|---|
| Basal | — | 0.71 | — | 1.39 | — | 1.96 | — |
| A41030 | 25 | 0.75 | 5.6 | 1.38 | −0.7 | 1.83 | 6.6 |
| A41030 | 50 | 0.77 | 8.5 | 1.38 | −0.7 | 1.78 | 9.2 |
| A41030 | 100 | 0.76 | 7.0 | 1.44 | 3.6 | 1.90 | 3.1 |

Thus in another aspect, this invention provides a method for promoting the growth of weanling pigs which comprises administering to the pigs in their diet a growth-promoting amount of the A41030 antibiotic complex, or an A41030 antibiotic factor, or a pharmaceutically-acceptable, non-toxic salt thereof. The method is preferably carried out by administering to the pigs between about 25 g. and about 200 g. of the A41030 antibiotic complex, or a pharmaceutically-acceptable, non-toxic salt thereof per ton of feed. The antibiotic A41030 complex, or the individual factors, in the form of a pharmaceutically-acceptable, non-toxic salt, can also be administered to the pigs in the drinking water.

The A41030 antibiotics are also useful for increasing the efficiency of feed utilization in ruminant animals. It is known that the efficiency of carbohydrate utilization in ruminants is increased by treatments which stimulate the animals' rumen flora to produce propionate compounds rather than acetate or butyrate compounds (for a more complete discussion, see Church et al. in "Digestive Physiology and Nutrition of Ruminants," Vol. 2, 1971, pp. 622 and 625).

The effectiveness of antibiotic A41030 complex and A41030 factor A for modifying the ratio of volatile fatty acids (VFA) produced in the rumen is shown by means of in vitro tests according to the procedure set forth hereinbelow.

Rumen fluid was obtained from a steer having a surgically-installed fistula opening into the rumen. The steer was maintained on a high-grain ration, the composition of which follows:

| 69.95% | coarse ground corn |
|---|---|
| 10% | ground corncobs |
| 8% | soybean meal (50% protein) |
| 5% | alfalfa meal |
| 5% | molasses |
| 0.6% | urea |
| 0.5% | dicalcium phosphate |
| 0.5% | calcium carbonate |
| 0.3% | salt |
| 0.07% | Vitamin A and $D_2$ premix |
| 0.05% | Vitamin E premix |
| 0.03% | trace mineral premix |

A sample of rumen fluid was strained through 4 layers of cheesecloth and the filtrate was collected in a vacuum bottle. The particulate matter retained by the cheesecloth was resuspended in enough physiological buffer to return it to the original volume of the rumen fluid, and the suspension was again strained through cheesecloth. The buffer used is described below:

| 0.316 g./liter | $Na_2HPO_4$ |
|---|---|
| 0.152 g./liter | $KH_2PO_4$ |
| 2.260 g./liter | $NaHCO_3$ |
| 0.375 g./liter | KCl |
| 0.375 g./liter | NaCl |
| 0.112 g./liter | $MgSO_4$ |
| 0.038 g./liter | $CaCl_2$ |
| 0.008 g./liter | $FeSO_4.7H_2O$ |
| 0.004 g./liter | $MnSO_4$ |
| 0.004 g./liter | $ZnSO_4.7H_2O$ |
| 0.002 g./liter | $CuSO_4.5H_2O$ |
| 0.001 g./liter | $CoCl_2$ |

Cheng et al., J. Dairy Sci. 38, 1225, (1955).

The two filtrates were pooled in a separatory funnel and allowed to stand till particulate matter rose to the top. The clear layer was then separated and diluted 1:1 with the same buffer, and adjusted to pH 7.0.

Ten ml. of the diluted rumen fluid thus prepared was placed in a 25 ml. flask with 90 mg. of finely-powdered high-grain ration, the composition of which is described above. The compound to be tested was weighed out and dissolved in the appropriate solvent, supra. The solution was placed on the finely-powdered ration in each test flask and dried.

Two sets of four untreated control flasks each were also prepared. One set of four untreated control flasks was incubated for 16 hours at 38° C. with the test flasks. The other set of four untreated control flasks were zero-time controls, the fermentation in which was stopped as soon as the flasks were prepared by addition of 2 ml. of 25 percent metaphosphoric acid to each flask.

Fermentation in the incubated test and control flasks was stopped at the end of 16 hours by addition of 2 ml. of 25 percent metaphosphoric acid to each flask.

All of the samples were allowed to settle, and the supernatant was analyzed by gas chromatographic methods for acetate, propionate, and butyrate.

The analysis for each volatile fatty acid found in the zero-time controls was substracted from the analyses of the untreated controls and of the test flasks. The resulting values reflect the amount of each VFA produced during the 16-hour fermentation period.

The data below are reported as the ratio of VFA's produced in treated flasks to VFA's produced in untreated control flasks. This method of reporting the data shows most clearly the results of the changes in the chemistry of the rumen brought about by the present novel method of feed utilization improvement. See Table 24, which follows.

TABLE 24

| Compound | Rate | Acetate | Propionate | Butyrate |
|---|---|---|---|---|
| A41030 | 5 mcg./ml. | 0.94 | 1.23 | 0.72 |
| A41030 | 5 mcg./ml. | 1.03 | 1.33 | 0.59 |
| A41030 | 5 mcg./ml. | 0.94 | 1.51 | 0.54 |
| A41030A | 2 mcg./ml. | 1.03 | 1.33 | 0.94 |
| A41030A | 1 mcg./ml. | 1.01 | 1.31 | 0.66 |

The data tabulated above shows that the antibiotics are effective in increasing propionate production in the rumen.

Administration of the antibiotic compounds useful in this method prevents and treats ketosis as well as improves feed utilization. The causative mechanism of ketosis is a deficient production of propionate compounds. A presently recommended treatment is administration of propionic acid or feeds which preferentially produce propionates. It is obvious that the method disclosed in this application, which method encourages propionate production from ordinary feeds, will reduce incidence of ketosis.

It has been found that the antibiotic compounds disclosed herein increase the efficiency of feed utilization in ruminant animals when administered in a propionate-increasing dose. The propionate-increasing dose can range from about 10 to about 120 g. per ton, preferably in the range of from about 40 to about 80 g. per ton. The antibiotics, individually, or as the whole complex, or as an economical, less-purified whole complex, are suitably administered by incorporation in the animal's feed.

However, the antibiotic compounds can be usefully administered in other ways. For example, they can be incorporated into tablets, drenches, boluses, or capsules, and dosed to the animals. Formulation of the antibiotic compounds in such dosage forms can be accomplished by means of methods well known in the veterinary pharmaceutical art. Each individual dosage unit should contain a quantity of the feed-efficiency-improving compound which has a direct relation to the proper daily dose for the animal to be treated.

Capsules are readily produced by filling gelatin capsules with any desired form of the desired antibiotic. If desired, the antibiotic can be diluted with an inert powdered diluent, such as a sugar, starch, or purified crystalline cellulose in order to increase its volume for convenience in filling capsules.

Tablets of the antibiotics are made by conventional pharmaceutical processes. In addition to the active ingredient, a tablet usually contains a base, a disintegrator, an absorbent, a binder, and a lubricant. Typical bases include lactose, fine icing sugar, sodium chloride, starch and mannitol. Starch is also a good disintegrator, as is alginic acid. Surface active agents such as sodium lauryl sulfate and dioctyl sodium sulphosuccinate are also sometimes used. Commonly used absorbents again include starch and lactose, while magnesium carbonate is also useful for oily substances. Frequently-used binders are gelatin, gums, starch, dextrin and various cellulose derivatives. Among the commonly-used lubricants are magnesium stearate, talc, paraffin wax, various metallic soaps, and polyethylene glycol.

The antibiotic compound can also be administered as a slow-payout bolus. Such boluses are made in the manner tablets are made, except that a means to slow the dissolving of the antibiotic is provided. Boluses are made to release for lengthy periods, and the slow dissolution is assisted by choosing a highly water-insoluble form of the antibiotic. A substance such as iron filings is added to raise the density of the bolus and keep it static on the bottom of the rumen.

Dissolution of the antibiotic is delayed by use of a matrix of insoluble materials in which the drug is embedded. For example, substances such as vegetable waxes, purified mineral waxes, and water-insoluble polymeric materials are useful.

Drenches of the antibiotics are prepared most easily by choosing a water-soluble form of the antibiotic. If an insoluble form is desired for some reason, a suspension may be made. Alternatively, a drench may be formulated as a solution in a physiologically-acceptable solvent such as a polyethylene glycol.

Suspensions of insoluble forms of the antibiotics can be prepared in nonsolvents such as vegetable oils such as peanut, corn, or sesame oil; in a glycol such as propylene glycol or a polyethylene glycol; or in water, depending on the form of the antibiotic chosen.

Suitable physiologically-acceptable adjuvants are necessary in order to keep the antibiotic suspended. The adjuvants can be chosen from among the thickeners, such as carboxymethylcellulose, polyvinylpyrrolidone, gelatin, and the alginates. Many classes of surfactants also serve to suspend antibiotics. For example, lecithin, alkylphenol polyethylene oxide adducts, naphthalenesulfonates, alkylbenzenesulfonates, and the polyoxyethylene sorbitan esters are useful for making suspensions in liquid nonsolvents.

In addition, many substances which affect the hydrophilicity, density, and surface tension of the liquid can assist in making suspension in individual cases. For example, silicone antifoams, glycols, sorbitol, and sugars can be useful suspending agents.

The suspendable antibiotic may be offered to the animal grower as a suspension, or as a dry mixture of the antibiotic and adjuvants to be diluted before use.

The antibiotics may also be administered in the drinking water of the ruminants. Incorporation into drinking water is performed by adding a water-soluble or water-suspendable form of the desired antibiotic to the water in the proper amount. Formulation of the antibiotic for addition to drinking water follows the same principles as formulation of drenches.

The most practical way to treat animals with these antibiotic compounds is by the formulation of the compounds into the feed supply. Any type of feed may be medicated with the antibiotic compounds, including common dry feeds, liquid feeds, and pelleted feeds.

The methods of formulating drugs into animal feeds are well known. It is usual to make a concentrated drug premix as a raw material for medicated feeds. For example, typical drug premixes may contain from about one to about 400 grams of drug per pound of premix. The wide range results from the wide range of concentration of drug which may be desired in the final feed. Premixes may be either liquid or solid.

The formulation of animal feeds containing the proper amounts of the antibiotic compounds for useful treatment is mainly a matter of arithmetic. It is necessary only to calculate the amount of compound which it is desired to administer to each animal, to take into account the amount of feed per day which the animal eats, and the concentration of antibiotic compound in the premix to be used, and calculate the proper concentration of antibiotic compound in the feed.

All of the methods of formulating, mixing, and pelleting feeds which are normally used in the ruminant or nonruminant feed art are entirely appropriate for manufacturing feeds containing the antibiotic compounds usable in this method.

It has also been found that antibiotic A41030 complex not only increases the efficiency of feed utilization in ruminants utilized for meat production (as described hereinbefore), but also causes a surprising improvement in milk production without an adverse effect on milk quality when administered to lactating animals having a developed rumen process.

The requirements and objectives of feed utilization of lactating ruminants such as dairy cows differ considerably from those of ruminants raised for meat production. Ruminal volatile fatty acid (VFA) production is of course of primary importance, since it relates directly to the normal maintenance of the animal, as well as to the quality and quantity of the milk produced by the animal. In the lactating ruminant, however, energy for lactation is the most limiting factor in milk production. Acetate is required for milk fat synthesis, while propionate is utilized to produce glucose, which in turn is required for lactose synthesis, and also has a minor role in milk fat production. Butyrate is more glycogenic than lipogenic, the lipogenic aspect being indirect since butyrate must first be degraded to acetate units before it can be utilized for long chain fatty acid synthesis, i.e., milk fat.

Accordingly, in order to increase milk production in lactating ruminants, it is necessary to increase propionate production, but not at a large expense of acetate and butyrate production. Significantly reduced acetate and butyrate levels result in drastically reduced milk fat content, thereby rendering milk production less efficient with respect to both quality and economically (bulk milk prices are determined in part by milk fat content).

The present improvement in milk production is manifested in increased protein content of the milk, without appreciable change of fat content. The method of accomplishing the improvement comprises orally administering to a lactating ruminant a propionate-increasing amount of antibiotic A41030 complex.

The antibiotic A41030 complex can be formulated for convenient oral administration to a ruminant, the formulation being as a feed pre-mix, a feed additive, a lick, a water additive, or if desired, the antibiotic A41030 complex can be formulated for slow release over a prolonged period of time following a single administration.

The antibiotic A41030 complex and factors A, B, C, D, E, F, and G can be isolated for use in the animal feeds described hereinbefore by the methods disclosed in the Examples set forth hereinafter. It is also possible, if desired, after the production of A41030 antibiotic activity, to simply dry the whole fermentation broth and mix the dried medium directly into the feed or feed premix.

Further, it is possible the hereindisclosed A41030 antibiotic complex and factors can be combined with a synthetic tanning agent which is a sulfited phenol formaldehyde syntan, such as is sold by A. J. & O. J. Pilar Inc. of Newark, N.J., under the tradename TruTan RT Regular. The combination of the antibiotic and the synthetic tanning agent, the antibiotic-syntan complex, can be used without separation of the constituents, in the animal feed supplement compositions described above.

As has been shown, antibiotic A41030 complex and A41030 factor A beneficially alter the production of propionates relative to the production of acetates in the rumen. The same treatment also benefits monogastric animals which ferment fibrous vegetable matter in the cecum. The monogastric animals here referred to are those which consume fibrous vegetable food and digest at least part of it by microbiological fermentation in the cecum. The cecal fermentation follows a chemical pathway similar to rumen fermentation.

Horses, swine, and rabbits are exemplary animals which digest a part of their food by cecal fermentation. The overall feed utilization of such animals is improved by the oral administration of these antibiotics which cause a beneficial change in the propionate/acetate ratio. Horses and rabbits are exemplary of animals in which cecal fermentation is a major part of the total digestive process, and in which these antibiotics are accordingly particularly beneficial.

The A41030 complex is produced by culturing the hitherto undescribed microorganism *Streptomyces virginiae* NRRL 12525, or by culturing the hitherto undescribed microorganism *Streptomyces virginiae* NRRL 15156, or an A41030-producing mutant or variant of either microorganism, in a culture medium containing assimilable sources of carbon, nitrogen, and inorganic salts, under submerged aerobic fermentation conditions until a substantial level of antibiotic activity is produced. Most of the antiobiotic activity is generally found in the broth, while minor amounts of antibiotic activity may be associated with the mycelia. The A41030 complex is most readily separated from the fermentation mixture by removal of the mycelia, i.e., the biomass, by filtration. The mycelia are generally discarded. The antibiotic complex is then isolated from the filtered fermentation broth preferably by column chromatography, over a suitable adsorbent using methanol:water (1:1) as the eluting agent.

Suitable adsorbents include carbon, alumina, anion and cation exchange resins, silica gel, polyamide, carboxymethylcelluloses, highly porous copolymers of styrene and divinylbenzene such as Diaion HP-20, the Amberlite XAD resins, and the Duolite resins such as ES-865 and the like, as well as Sephadex resins, the hydrophilic, insoluble, molecular-sieve chromatographic mediums made by cross-linking dextran, and also TSK Gels. The Diaion resins are a product of Mitsubishi Chemical Industries, Limited, Tokyo, Japan. The Amberlite XAD resins are produced by Rohm and Haas, Philadelphia, Pa. The Duolite resins are products of Diamond Shamrock, Redwood City, Calif. Sephadex resins are manufactured by Pharmacia Fine Chemicals AB, Uppsala, Sweden. The TSK Gels are available from E. Merck, Darmstadt, and from Bio-Rad, 2200 Wright Ave., Richmond, Calif., 94804.

The A41030 antibiotic complex can be further purified and separated into its individual factors by chromatographic techniques.

A number of different media may be used with *Streptomyces virginiae* NRRL 12525, or *Streptomyces virginiae* NRRL 15156, to produce the A41030 complex. For economy in production, optimal yield, and ease of product isolation, however, certain culture media are preferred. These media should contain assimilable sources of carbon, nitrogen, and inorganic salts. Suitable carbon sources include dextrin, starch, mannose, glycerol, and cottonseed oil. Optimum levels of carbon sources are from about 2 to about 3 percent by weight.

Preferred nitrogen sources include soybean grits, soybean flour, peanut meal, fish meal, meat peptone, and pork blood meal.

Essential trace elements necessary for the growth and development of the organism may occur as impurities in other constituents of the media in amounts sufficient to meet the growth and biosynthetic requirements of the organism. However, it may be beneficial to incorporate in the culture media additional soluble nutrient inorganic salts capable of yielding sodium, potassium, magnesium, calcium, ammonium, chloride, carbonate, phosphate, sulfate, nitrate and like ions.

Addition to the fermentation medium of Tween 80 (oily liquid polyoxyethylene sorbitan monooleate, a product of ICI Americas, Inc., Wilmington, Del.), at a level of 2-4% serves to increase the yield by about 300%. However, difficulty is experienced in isolating the A41030 antibiotic under these conditions.

Although small quantities of the A41030 antibiotic may be obtained by shake-flask culture, submerged aerobic fermentation in tanks is preferred for producing substantial quantities of the A41030 antibiotic. For tank fermentation, it is preferable to use a vegetative inoculum. The vegetative inoculum is prepared by inoculating a small volume of culture medium with the spore form, or mycelial fragments, to obtain a fresh, actively growing culture of the organism. The vegetative inoculum is then transferred to a larger tank where, after a suitable incubation time, the A41030 antibiotic is produced in optimal yield.

An alternate method of providing inoculum for the vegetative medium consists of substituting a lyophilized pellet for the aqueous spore suspension. Lyophilized pellets are prepared in a manner known in the art. Preparation of the spore suspension for lyophilization is similar to the preparation of the aqueous spore suspension, except that sterile calf serum is substituted for sterile distilled water.

The A41030-producing organism can be grown over a broad temperature range of from about 10° to about 34° C. Optimum production of A41030 antibiotic complex appears to occur at a temperature of about 30° C.

As is customary in aerobic submerged culture processes, sterile air is dispersed through the culture medium. For efficient growth of the organism, the volume of the air used in tank production is in the range of from about 0.1 to about 0.5 volumes of air per volume of culture medium per minute (v/v/m), with from about 100 to about 300 RPM agitation. An optimum rate in a 165-liter vessel containing 100 liters of fermentation medium is about 0.25 v/v/m, with agitation provided by an impeller rotating at about 200 RPM.

Antibiotic activity is generally present after about 48 hours and remains present for at least 144 hours during the fermentation period. Peak antibiotic production occurs at from about 96 hours to about 120 hours fermentation time.

Production of the A41030 antibiotic can be monitored during the fermentation by either agar diffusion using *B. subtilis*, or a turbidimetric method using *Staphylococcus aureus* ATCC 9114.

The antibiotic complex, and individual factors thereof, provided by this invention are produced by either *S. virginiae* NRRL 15156 or *S. virginiae* NRRL 12525 under fermentation conditions of temperature, duration, and media ingredients which are substantially equivalent. However, it appears that under such conditions, *S. virginiae* NRRL 12525 produces the antibiotic complex in somewhat greater abundance.

In order to illustrate more fully the operation of this invention, the following Examples are provided.

EXAMPLE 1

Preparation of First Stage Inoculum

The following medium was prepared for use in the agar slant culture of both *Streptomyces virginiae* NRRL 12525, and *Streptomyces virginiae* NRRL 15156:

| Ingredient | Amount (g/L.) |
| --- | --- |
| Dextrin[1] | 10.0 |
| Yeast extract | 1.0 |
| Enzyme-hydrolyzed casein[2] | 2.0 |
| Beef extract | 1.0 |
| $CoCl_2.6H_2O$ | 0.01 |
| Agar | 20.0 |
| Deionized water q.s. | to 1 liter |

[1]Matheson Coleman & Bell, Norwood, Ohio 45212
[2]N—Z—Amine A (Humko Sheffield Chemical Co., Memphis, Tenn.).

The pH of the medium as prepared was 6.5, and was adjusted to 7.3 using 5N aqueous sodium hydroxide before autoclaving. After autoclaving, the pH of the medium was 6.9.

In the case of each microorganism, the spores were inoculated on an agar slant made up of the aboveidentified ingredients, and the thus-inoculated slant was incubated for about six days at a temperature of about 30° C. The mature slant culture was then covered with sterile distilled water and scraped with a sterile tool to loosen the spores and the mycelium. One milliliter of the resulting spore suspension was used to inoculate 50 ml. of vegetative medium. An alternate method of providing inoculum for the vegetative medium consisted of substituting a lyophilized pellet for the aqueous spore suspension. The composition of the vegetative medium for NRRL 15156 was as follows:

| Ingredient | Amount (g/L.) |
| --- | --- |
| Glucose | 15.0 |
| Dextrin | 20.0 |
| Soybean grits (or soybean flour) | 15.0 |
| Corn steep liquor | 10.0 |
| $CaCO_3$ | 2.0 |
| Tap water | q.s. to 1 liter |

The unadjusted pH of the medium was 5.5, which was adjusted to pH 6.5 with 5N aqueous sodium hydroxide before autoclaving. The pH of the medium after autoclaving was 7.0.

The composition of the vegetative medium for NRRL 12525 was as follows:

| Ingredient | Amount (g./L.) |
| --- | --- |
| Glucose | 20.0 |
| Soybean grits (or soybean flour) | 15.0 |
| Corn steep liquor | 10.0 |
| $CaCO_3$ | 2.0 |
| Tap water | q.s. to 1 liter |

The unadjusted pH of the medium was 5.5, which was adjusted to pH 6.5 with 5N aqueous sodium hydroxide before autoclaving. The pH of the medium after autoclaving was 7.0.

In the case of each microorganism, the vegetative inoculum was incubated in a 250 ml. widemouth Erlenmeyer flask containing 50 ml. of medium at about 30° C. for about 48 hours on a shaker rotating through an arc 2 inches in diameter at 250 RPM. This incubated medium is used either to inoculate small fermenters (the inoculum being approximately 1% per volume of fermenter medium) or to inoculate a second stage medium having the same composition as the vegetative medium for the production of a larger volume of culture.

Fermentation of NRRL 15156

Fifty milliliters of a production medium was inoculated with 1% (0.5 ml.) of the incubated vegetative medium from above. The production medium had the following composition:

| Ingredient | Amount (g/L.) |
| --- | --- |
| Dextrin[1] | 30.0 |
| Soybean grits | 6.0 |
| $K_2HPO_4$ | 1.0 |
| $FeSO_4.7H_2O$ | 0.005 |
| $MgSO_4.7H_2O$ | 1.0 |
| $NaNO_3$[2] | 1.0 |
| $CaCO_3$ | 2.0 |
| Deionized water | q.s. to 1 liter |

[1]The dextrin may be either tapioca or potato dextrin.
[2]For the fermentation of NRRL 12525, the concentration of $CaCO_3$ was 4.0 g./L.

The $K_2HPO_4$ was dissolved in water, the solution sterilized separately, and the requisite amount of the solution added to the other ingredients of the medium that had been autoclaved.

The inoculated fermentation medium, 50 ml., was incubated in a 250-ml. Erlenmeyer flask at about 30° C. for about 4–5 days on a shaker rotating through an arc 2 inches in diameter at 250 RPM.

The *Streptomyces virginiae* NRRL 12525 was also incubated in a fermentation carried out on a larger scale in 165-liter and 1600 gallon tanks using the production medium described immediately hereinabove.

The inoculated production medium was allowed to ferment in a 165-liter fermentation tank containing 100 liters of medium for about 210 hours (8.75 days) at a temperature of about 32° C. The fermentation medium was aerated with sterile air at a rate of 0.25 v/v/m and was stirred with conventional agitators at about 200 RPM.

The large scale fermentation of NRRL 12525 was the source of the broth from which the A41030 antibiotics were separated, as described hereinafter.

EXAMPLE 2

Separation of A41030 Antibiotics

Whole fermentation broth (4215 liters), obtained as described in Example 1, was filtered using a filter aid (Hyflo Supercel, a diatomaceous earth, Johns-Manville Products Corporation) in a filter press. The filtered broth was applied to a column containing 100 L. of Diaion HP-20 (a highly porous styrenedinvinylbenzene copolymer in bead form, Mitsubishi Chemical Industries, Limited, Tokyo, Japan) at a flow rate of 4 L./min. The column was washed successively with 300 L. of water and 1000 L. of methanol:water (1:3) at a rate of 4 L./min. Elution was performed with methanol:water (1:1) at the rate of 6 L./min., collecting 100-L. fractions. Each fraction was analyzed for biological activity. The bioassay was performed by a paper disc assay on agar plates seeded with *Bacillus subtilis*. Fraction 1 was discarded. Fractions 2–15, inclusive, were combined, concentrated under reduced pressure, and the concentrate lyophilized to give 220 g. of crude antibiotic complex.

A portion of this complex, 110 g., was dissolved in 5 L. of methanol:water (1:1), by adjustment to pH 10 with aqueous sodium hydroxide, and the mixture was filtered. The filtrate was applied at 50 ml./min. to a 30-L. column (0.2×1 m.) of coarse Sephadex G-50 (a hydrophilic, insoluble, molecular-sieve chromatographic medium, made by cross linking dextran, and sold by Pharmacia Fine Chemicals, Piscataway, NJ 08854), previously equilibrated with methanol:water (1:1). The column was eluted with methanol:water (1:1) at 50 ml/min., collecting 3-L. fractions. Fractions 1–12, inclusive, were discarded. Fractions 13–24, inclusive, which contained activity against *B. subtilis*, were combined, concentrated under reduced pressure, and lyophilized to give 35.7 g. of the A41030 antibiotic complex.

EXAMPLE 3

Isolation of A41030 Factor A

An 8 g. portion of the A41030 complex form Example 2 was dissolved in 200 ml. of a solvent consisting of water:acetonitrile:sodium chloride (84:16:2 g./L.) and filtered. The filtrate was applied to a stainless steel column (8×100 cm.) packed with 4 L. of 10–20 micron LP-1/$C_{18}$ reversed-phase silica gel which was prepared in our laboratories by a special procedure described in Examples 6 and 7 of U.S. Pat. No. 4,299,763 (Nov. 10, 1981), which published description is hereby incorporated into and made a part of the instant application. The column was part of a Chromatospac Prep-100 unit (Jobin Yvon, 16–18 Rue du Canal 91160 Longjumeau, France). The column was eluted at 60 ml./min. with water:acetonitrile:sodium chloride (84:16:2 g./L.) collecting 480-ml. fractions. The eluate was monitored at 254 nm using an ISCO Model UA-5 UV monitor with a Type 6 optical unit (Instrumentation Specialties Co., Lincoln, NE 68505). Selected fractions were analyzed for the presence of Factor A by analytical high performance liquid chromatography (HPLC) on a 4.6×250 mm. stainless steel column packed in our laboratories with 10 micron LP-1/$C_{18}$ which was prepared in our laboratories by the special procedure described above. The sample was applied with a Rheodyne Model 7120 injection valve (Rheodyne Inc., Berkeley, CA 94710). The solvent, consisting of water:acetonitrile:sodium acetate (81:19:0.03M) adjusted to pH 6 with glacial acetic acid, was supplied at 1 ml./min. (1200 psi) by a Milton Roy Duplex Minipump (Laboratory Data Control, Division of Milton Roy Co., Rivera Beach, FL 33404). Factor A was detected at 254 nm using an ISCO Model UA-5 UV detector. Fractions 1–51, inclusive, were discarded. Fractions 52–79, inclusive, rich in factor A were combined and concentrated under reduced pressure to a volume of 500 ml. The concentrate was adjusted to pH 8.2 with aqueous sodium hydroxide and filtered. The filtrate was applied at 15 ml./min. to 100 ml. of Diaion HP-20 resin in a column (2.8×22 cm.), previously equilibrated with water. The column was washed with water (400 ml. adjusted to pH 2.5 with formic acid) until no chloride was detected in the wash by precipitation as silver chloride. Elution was performed with water:acetonitrile (8:2) at 15 ml./min., collecting 1 L. fractions. Fractions were analyzed for activity against *B. subtilis*. Crystalline factor A, which formed in fraction 2 upon refrigeration, was recovered by filtration (389.6 mg.). Fraction 1 and the filtrate from fraction 2 were each concentrated under reduced pressure and lyophilized to give 731.8 mg. and 514 mg. of factor A, respectively.

EXAMPLE 4

Isolation of A41030 Factor B

A 1.0 g. portion of the A41030 complex was dissolved in 35 ml. of a solvent consisting of water:acetonitrile:sodium chloride (85:15:2 g./L.) and the solution was applied to a 4.7×45 cm. Michel-Miller high-performance-low-pressure-liquid-chromatography (HPLPLC) glass column (Ace Glass, Inc., Vineland, NJ 08360) packed in our laboratories with 25-40 micron LiChroprep RP-18 [hydrocarbon phase ($C_{18}$) chemically bonded to silica gel, from MC/B Manufacturing Chemists, Inc., Cincinnati, OH]. An FMI valveless piston pump (Fluid Metering Inc., Oyster Bay, NY 11771) was used to elute the column at 21 ml./min. (100 psi), with the same solvent combination used for sample dissolution, collecting 21-ml. fractions. The eluate was monitored at 280 nm using an ISCO Model UA-5 UV detector. Fractions 1–183, inclusive, were discarded. Fractions 184–245, inclusive, rich in factor B, were combined and concentrated under reduced pressure to 25 ml. Concentrates from seven similar purifications were combined, diluted to 1.4 L. with water, and applied at 8–10 ml./min. to 100 ml. of Diaion HP-20 resin in a column, previously equilibrated with water. The column was washed with water (600 ml.) until no chloride was detected in the wash by precipitation as silver chloride. Elution was performed with water:methanol (1:1) at 8–10 ml./min., collecting 300 ml. fractions. Fractions were analyzed for activity against *B. subtilis*. Fractions 1–5 were combined, concentrated under reduced pressure, and lyophilized to give 523 mg. of crude factor B.

A 550 mg. portion of two combined crude preparations of factor B was dissolved in 10 ml. of a solvent consisting of water:acetonitrile:dibutylamine (75:25:0.03M, which solvent had been adjusted to pH 7.8 with phosphoric acid) by addition of tetrabutylammonium hydroxide until solution had been accomplished. The solution was applied to a 2.8×59 cm. Michel-Miller HPLPLC glass column packed with 25-40 micron LiChroprep RP-8 [hydrocarbon phase ($C_8$) chemically bonded to silica gel, from MC/B Manufacturing Chemists, Inc., Cincinnati, OH]. Using an FMI pump, the column was eluted at 5 ml./min. (35 psi) with the same solvent combination used for sample dissolution. The eluate was monitored at 254 nm using an ISCO Model UA-5 UV detector. Selected 27-ml. fractions were analyzed for the presence of factor B by analytical HPLC on a 4.6×250 mm. stainless steel column packed with 10 micron LiChrosorb RP-18 (a commercially available, reversed-phase silica gel, manufactured by E. Merck, Darmstadt, Germany). The sample was applied using a Rheodyne Model 7120 injection valve. The solvent, consisting of water:acetonitrile:dibutylamine (82:18:0.03M) adjusted to pH 2.5 with phosphoric acid, was supplied at 1 ml./min. (750 psi) by a Constametric III pump (LDC-Laboratory Data Contol, Division of Milton Roy Co., Riviera Beach, FL 33404). Factor B was detected at 225 nm using an LDC Spectro Monitor III variable wavelength UV detector. The portion of the RP-8 column eluate from 999–1296 ml., rich in factor B, was concentrated to a volume of 200 ml. The concentrate was diluted to a volume of 500 ml., adjusted to pH 2.0 with phosphoric acid, and sodium chloride (1 mg./ml.) was added as an ionic marker. This solution was applied at 20 ml./min. to 100 ml. of Diaion HP-20 resin in a column (2.8×22 cm.), previously equilibrated with water. The column was washed with water (500 ml.) adjusted to pH 2.5 with aqueous formic acid, until no chloride was detected in the wash by precipitation as silver chloride. The column was then eluted with 1 L. of water:acetonitrile (6:4) at 30 ml./min. The eluate was concentrated under reduced pressure and lyophilized to give 295.6 mg. of crude factor B.

A 285 mg. portion of this preparation was dissolved in 30 ml. dimethylformamide:water (4:6) by heating, cooled to room temperature, and refrigerated, resulting in precipitation of factor B. The precipitate was recovered by filtration, washed with acetone, and dried under vacuum, to yield 84 mg. of factor B.

EXAMPLE 5

Isolation of A41030 Factor C

A 9.0 g. portion of the A41030 complex was dissolved in 200 ml. of a solvent consisting of water:acetonitrile:sodium chloride (83:17:2 g./L.) and the solution was filtered. The filtrate was applied to an 8×100 cm. stainless steel column packed with 4 L. of 10–20 micron LP-1/$C_{18}$ reversed:phase silica gel which was prepared in our laboratories by the special procedure described in Example 3. The column, part of a Chromatospac Prep-100 unit, was eluted at 60 ml./min. with the same solvent combination used for sample dissolution, and 480-ml. fractions were collected. The eluate was monitored at 254 nm using an ISCO Model UA-5 UV detector. Selected fractions were analyzed for the presence of factor C by analytical HPLPLC on an 0.8×30 cm. Michel-Miller glass column packed in our laboratories with 25-40 micron LiChroprep RP-8. The solvent, water:acetonitrile:sodium chloride (84:16:2 g./L.), was supplied at 4 ml./min. by an FMI pump. Factor C was detected at 254 nm using an ISCO Model UA-5 UV detector. Fractions 1–27, inclusive, were discarded. Fractions 28–52; inclusive, rich in factor C, were combined and concentrated under reduced pressure to a volume of 500 ml.

Concentrates from two similar purifications were combined, filtered, and applied at 10 ml./min. to 100 ml. of Diaion HP-20 resin in a column (2.8×22 cm.), previously equilibrated with water. The column was washed with water (2 L.) until no chloride was detected in the wash by precipitation as silver chloride. Elution was performed with 1 L. of water:acetonitrile (6:4) at 15 ml./min. The eluate was concentrated under reduced pressure and lyophilized to give 2.75 g. of a factor C-enriched mixture of factors. A 1.25 g. portion of this mixture was dissolved in 25 ml. of a solvent consisting of water:acetonitrile:dibutylamine (80:20:0.3M, which solvent had been adjusted to pH 7.8 with phosphoric acid) by addition of tetrabutylammonium hydroxide until solution had been accomplished. The sample was applied to a 2.8×59 cm. Michel-Miller glass column packed with 25–40 micron LiChroprep RP-8 and the column was eluted at 4 ml./min., using an FMI pump, with the same solvent combination used for sample dissolution. The eluate was monitored at 254 nm using an ISCO Model UA-5 UV detector. Selected 28-ml. fractions were analyzed for the presence of factor C by analytical HPLC on a 4.6×150 mm. stainless steel column packed in our laboratories with 10 micron Nucleosil $C_{18}$ (a commercially available, reversed-phase silica gel, manufactured by Rainin Instrument Co., Inc., Woburn, MA 01801). The sample was applied using a Rheodyne Model 7120 injection valve. The solvent, consisting of water:acetonitrile:sodium acetate (81:19:2 g./L.) adjusted to pH 6 with glacial acetic acid, was supplied at 1 ml./min. by a Milton Roy Duplex Minipump. Factor C was detected at 225 nm using an ISCO Model 1800 variable wavelength UV detector. The portion of the eluate from 4.2–5.1 L., rich in factor C, was concentrated under reduced pressure to a volume of 500 ml.

Concentrates from three similar purifications were combined and dissolved by addition of phosphoric acid to pH 1.7. Sodium chloride (1 mg./ml.) was added as an ionic marker. The sample was applied at 20 ml./min. to 100 ml. of Diaion HP-20 resin in a column (2.8×22 cm.), previously equilibrated with water. The column was washed with aqueous formic acid of pH 2.5 (300 ml.), until no chloride was detected in the wash by precipitation as silver chloride. The column was eluted with 1 L. of water:acetonitrile (6:4) at 30 ml./min. The eluate was collected, concentrated under reduced pressure, and lyophilized to give 0.87 g. of partially purified factor C. This preparation was dissolved in 20 ml. of a solvent consisting of water:acetonitrile:dibutylamine (80:20:0.03M, which solvent had been adjusted to pH 7.8 with phosphoric acid) by addition of tetrabutylammonium hydroxide until solution had occurred. The sample was chromatographed on 25–40 micron LiChroprep RP-8 in a 2.8×59 cm. Michel-Miller glass column, as previously described. The portion of the eluate from 2.45–3.20 L. was concentrated under reduced pressure to a volume of 500 ml.

Concentrates from two similar purifications were combined and desalted on a column containing Diaion HP-20 resin in the fashion previously described. The eluate was concentrated under reduced pressure and lyophilized to give 688 mg. of factor C. A 678 mg. portion of this preparation was dissolved in 60 ml. water:acetonitrile (6:4) by heating. The solution was cooled and factor C precipitated upon refrigeration. The precipitate was recovered by filtration, washed with acetone, and dried under vacuum to give 428 mg. of factor C.

EXAMPLE 6

Isolation of A41030 Factor D

A 6.0 g. portion of the A41030 complex was dissolved in 200 ml. of a solvent consisting of water:acetonitrile:sodium chloride (83:17:2 g./L.) and the solution filtered. The filtrate was applied to an 8×100 cm. stainless steel column packed with 4 L. of 10–20 micron LP-1/$C_{18}$ reversed-phase silica gel which was prepared in our laboratories by the special procedure described in Example 3. The column, part of a Chromatospac Prep-100 unit, was eluted at 60 ml./min., with the same solvent combination used for sample dissolution, and 480-ml. fractions were collected. The eluate was monitored at 254 nm using an ISCO Model UA-5 UV detector. Selected fractions were analyzed for the presence of Factor D by analytical HPLPLC on an 0.8×30 cm. Michel-Miller glass column packed in our laboratories with 25–40 micron LiChroprep RP-8. The solvent, water:acetonitrile:sodium chloride (84:16:2 g./L.), was supplied at 4 ml./min. using an FMI pump. Factor D was detected at 254 nm using an ISCO Model UA-5 UV detector. Fractions 1–34, inclusive, were discarded. Fractions 35–53, inclusive, rich in factor D, were combined and concentrated under reduced pressure to a volume of about 500 ml.

Concentrates from two similar purifications were combined, diluted to 3 L. with water, and applied at 8–10 ml./min. to 100 ml. of Diaion HP-20 resin in a column (2.8×22 cm.), previously equilibrated with water. The column was washed with water (300 ml.) until no chloride was detected in the wash by precipitation as silver chloride. Elution was performed with 1 L. of a solvent consisting of water:acetonitrile (6:4) at 8–10 ml./min. The eluate was concentrated under reduced pressure and lyophilized to give 2.33 g. of a factor D-enriched mixture of factors.

A 1.15 g. portion of this mixture was dissolved in 25 ml. of a solvent consisting of water:acetonitrile:dibutylamine (80:20:0.03M, which solvent had been adjusted to pH 7.8 with phosphoric acid) by addition of tetrabutylammonium hydroxide until solution occurred. The sample was applied to a 2.8×59 cm. Michel-Miller glass column packed with 25–40 micron LiChroprep RP-8, and the column was eluted at 5 ml./min., using an FMI pump, with the same solvent combination used for sample dissolution. The eluate was monitored at 254 nm using an ISCO Model UA-5 UV detector. Selected 25 ml. fractions were analyzed for the presence of factor D by analytical HPLC on a 4.6×25 mm. stainless steel column packed with 10 micron LiChrosorb RP-18 (a commercially available, reversed-phase silica gel, manufactured by E. Merck, Darmstadt, Germany). The sample was applied using a Rheodyne Model 7120 injection valve. The solvent, consisting of water:acetonitrile:dibutylamine (80:20:0.03M) adjusted to pH 2.5 with phosphoric acid, was supplied at 0.75 ml./min. using a Milton Roy Duplex Minipump. Factor D was detected at 225 nm using an ISCO Model 1800 variable wavelength UV detector. The portion of the eluate from 2.6–3.4 L., rich in factor D, was concentrated under reduced pressure to a volume of 300 ml.

Concentrates from three similar purifications were combined and dissolved by addition of phosphoric acid to pH 7.7. Sodium chloride (1 mg./ml.) was added as an ionic marker. The sample was applied at 20 ml./min. to 100 ml. of Diaion HP-20 resin in a column (2.8×22 cm.), previously equilibrated with water. The column was washed with water (300 ml.) adjusted to pH 2.5 with aqueous formic acid, until no chloride was detected in the wash by precipitation as silver chloride. The column was eluted with 1 L. of water:acetonitrile (6:4) at 30 ml./min. The eluate was concentrated under reduced pressure and lyophilized to give 0.63 g. of partially purified factor D. This preparation was dissolved in 15 ml. of a solvent consisting of water:acetonitrile:dibutylamine (80:20:0.03M, which solvent had been adjusted to pH 7.8 with phosphoric acid) by addition of tetrabutylammonium hydroxide until solution occurred. The solution was chromatographed on 25-40 micron LiChroprep RP-8 in a 2.8×59 cm. Michel-Miller glass column, in the manner previously described. The portion of the eluate from 2.5-3.0 L. was concentrated under reduced pressure to a volume of about 200 ml. This concentrate was desalted on a column containing Diaion HP-20 resin in the fashion previously described. The eluate was concentrated under reduced pressure and lyophilized to give 193 mg. of partially-purified factor D.

A 259 mg. portion of two combined partially purified factor D preparations was dissolved in 6 ml. of a solvent consisting of water:acetonitrile:dibasic sodium phosphate (82:18:0.03M, which solvent had been adjusted to pH 7.8 with phosphoric acid) and adjusted to pH 10 by addition of aqueous 5N NaOH. The solution was applied to a 2.8×59 cm. Michel-Miller glass column packed with 25-40 micron LiChroprep RP-8, and the column was eluted at 4 ml./min., using an FMI pump, with the same solvent combination used for sample dissolution. The eluate was monitored at 254 nm using an ISCO Model UA-5 UV detector. Selected 27-ml. fractions were analyzed for the presence of factor D by analytical HPLC on a 4.6×150 mm. stainless steel column packed in our laboratories with 10 micron Nucleosil $C_{18}$. The sample was applied using a Rheodyne Model 7120 injection valve. The same solvent combination used for the preparative elution was supplied at 0.6 ml./min. by a Milton Roy Duplex Minipump. Factor D was detected at 225 nm using an ISCO Model 1800 variable wavelength UV detector. The portion of the eluate from 405-1134 ml. was concentrated under reduced pressure to a volume of 500 ml., and desalted on a column containing Diaion HP-20 resin in the fashion previously described. The eluate was concentrated under reduced pressure and lyophilized to give 120 mg. of factor D.

EXAMPLE 7

Isolation of A41030 Factor E

A 0.3 g. portion of the A41030 complex was dissolved in 30 ml. of a solvent consisting of water:acetonitrile:sodium chloride (85:15:2 g./L.), and applied to a 2.8×59 cm. Michel-Miller glass column packed in our laboratories with 25-40 micron LiChroprep RP-8. An FMI pump was used to elute the column at 12 ml./min. (85 psi), with the same solvent combination used for sample dissolution, collecting 24-ml. fractions. The eluate was monitored at 254 nm using an ISCO Model UA-5 UV detector. Fractions 1-54, inclusive, were discarded. Fractions 55-122, inclusive, rich in factor E, were combined and concentrated under reduced pressure to a volume of 50 ml.

Concentrates from 13 similar purifications were combined, diluted to 1.5 L. with water, and applied at 5 ml./min. to 100-ml. of Diaion HP-20 resin in a column (2.8×22 cm.), previously equilibrated with water. The column was washed with water (900 ml.) until no chloride was detected in the wash by precipitation as silver chloride. Elution was then performed with water:methanol (1:1) at 10 ml./min., collecting 300-ml. fractions. Fractions were analyzed for activity against *B. subtilis.* Fractions 1-8, inclusive, were combined, concentrated under reduced pressure, and lyophilized to give 1.04 g. of a factor E-enriched mixture of factors. A 0.5 g. portion of this mixture was dissolved in 10 ml. of a solvent consisting of water:acetonitrile:sodium chloride (84:14:2 g./L.), and applied to a 2.8×59 cm. Michel-Miller glass column packed with 25-40 micron LiChroprep RP-8. An FMI pump was used to elute the column at 5 ml./min., with the same solvent combination used for sample dissolution, and 25-ml. fractions were collected. The eluate was monitored at 254 nm using an ISCO Model UA-5 UV detector. Selected fractions were analyzed for the presence of factor E by analytical HPLC on a 4.6×150 mm. stainless steel column packed in our laboratories with 5 micron ODS-Hyperspheres (Shandon Southern Products, Ltd., Cheshire, England). The sample was applied using a Rheodyne Model 7120 injection valve. The solvent, consisting of water:acetonitrile:sodium acetate (81:19:2 g./L.) adjusted to pH 6 with glacial acetic acid, was supplied at 0.65 ml./min. by a Milton Roy Duplex Minipump. Factor E was detected at 225 nm using an ISCO Model 1800 variable wavelength UV detector. The portion of the eluate from 1520-1780 ml. was concentrated under reduced pressure to a volume of 50 ml.

Concentrates from three similar purifications were combined, diluted to 1 L. with water, and applied at 10 ml./min. to 100-ml. of Diaion HP-20 resin in a column (2.8×22 cm.), previously equilibrated with water. The column was washed with water (200 ml.) adjusted with aqueous formic acid to pH 2.5, until no chloride was detected in the wash by precipitation as silver chloride. Elution was performed with 0.5 L. of water:acetonitrile (6:4) at 15 ml./min. The eluate was concentrated under reduced pressure and lyophilized to give 202.2 mg. of partially purified factor E. This preparation was dissolved in 4 ml. of a solvent consisting of water:acetonitrile:sodium chloride (86:14:2 g./L.) and chromatographed at 4 ml./min. on a 2.8×59 cm. Michel-Miller glass column, packed with 25-40 micron LiChroprep RP-8, as previously described. The portion of the eluate from 2060-2480 ml., rich in factor E, was concentrated under reduced pressure to a volume of 50 ml. Concentrates from three similar purifications were combined and desalted on 100-ml. of Diaion HP-20 resin in a column, as previously described. The eluate was concentrated under reduced pressure and lyophilized to give 242 mg. of factor E.

EXAMPLE 8

Isolation of A41030 Factor F

A 9.0 g. portion of the A41030 complex was dissolved in 200 ml. of a solvent consisting of water:acetonitrile:sodium chloride (83:17:2 g./L.) and the solution was filtered. The filtrate was applied to an 8×100 cm. stainless steel column packed with 4 L. of 10-20 micron LP-1/$C_{18}$ reversed-phase silica gel which was prepared in our laboratories by the special procedure described in Example 3. The column, part of a Chromatospac Prep-100 unit, was eluted at 60 ml./min., with the same solvent combination used for sample dissolution, and 480- ml. fractions were collected. The eluate was monitored at 254 nm using an ISCO Model UA-5 UV detector. Selected fractions were analyzed for the presence of factor F by analytical HPLPLC on an 0.8×30 cm. Michel-Miller glass column packed in our laboratories with 25-40 micron LiChroprep RP-8. The solvent, water:acetonitrile:sodium chloride (84:16:2 g./L.), was supplied at 4 ml./min. by an FMI pump. Factor F was detected at 254 nm using and ISCO Model UA-5 UV detector. Fractions 1-25, inclusive, were discarded. Fractions 26-36, inclusive, rich in factor F, were combined and concentrated under reduced pressure to a volume of about 500 ml.

Concentrates from three similar purifications were combined, filtered, and the filtrate applied at 10 ml./min. to 100-ml. of Diaion HP-20 resin in a column (2.8×22 cm.), previously equilibrated with water. The column was washed with water (900 ml.) until no chloride was detected in the wash by precipitation as silver chloride. Elution was performed with 1 L. of water:acetonitrile (6:4) at 15 ml./min. The eluate was concentrated under reduced pressure and lyophilized to give 2.6 g. of partially purified factor F. A 500 mg. portion of this preparation was dissolved in 10 ml. of a solvent consisting of water:acetonitrile:sodium chloride (84:16:2 g./L.), by adjustment to pH 7.0 with aqueous sodium hydroxide. The solution was applied to a 4.7×45 cm. Michel-Miller glass column packed in our laboratories with 25-40 micron LiChroprep RP-18. An FMI pump was used to elute the column at 6 ml./min., with the same solvent combination used for sample dissolution, and 24-ml. fractions were collected. The eluate was monitored at 254 nm using an ISCO Model UA-5 UV detector. Selected fractions were analyzed for the presence of factor F, using the analytical HPLPLC system previously described. The portion of the eluate from 1940-2520 ml., rich in factor F was concentrated under reduced pressure to a volume of about 300 ml.

Concentrates from two similar purifications were combined and applied at 10 ml./min. to 100-ml. of Diaion HP-20 resin in a column (2.8×22 cm.), previously equilibrated with water. The column was washed with water (300 ml.) adjusted to pH 2.5 with formic acid, until no chloride was detected in the wash by precipitation as silver chloride. Elution was performed with 0.75 L. of water:acetonitrile (6:4). The eluate was concentrated under reduced pressure and lyophilized to give 299 mg. of factor F.

EXAMPLE 9

Isolation of A41030 Factor G

An 8 g. portion of the A41030 complex from Example 2 was dissolved in 200 ml. of a solvent consisting of water:acetonitrile:sodium chloride (84:16:2 g./L.) and filtered. The filtrate was applied to a stainless steel column (8×100 cm.) packed with 4 L. of 10-20 micron LP-1/$C_{18}$ reversed-phase silica gel which was prepared in our laboratories by the special procedure described in Example 3. The column was part of a Chromatospac Prep-100 unit (see Example 3). The column was eluted at 60 ml./min. with water:acetonitrile:sodium chloride (84:16:2 g./L.), collecting 480-ml. fractions. The eluate was monitored at 254 nm as described in Example 3. Selected fractions were analyzed for the presence of factor G by an analytical high performance liquid chromatography (HPLC) procedure described in preceding Examples.

Fractions 22-35, inclusive, rich in factor G, were combined and concentrated under reduced pressure to a volume of 500 ml. Concentrates from three similar purifications were combined, adjusted to pH 8.5 with aqueous sodium hydroxide, and filtered. The filtrate was applied at 10 ml./min. to 100 ml. of Diaion HP-20 resin in a column (2.8×22 cm), previously equilibrated with water. The column was washed with water (400 ml. adjusted to pH 2.5 with formic acid) until no chloride was detected in the wash by precipitation as silver chloride. Elution was performed with water:acetonitrile (6:4) at 15 ml./min., collecting 1 L. fractions. Fractions were analyzed for activity against *B. subtilis*. The active fractions were combined, concentrated under reduced pressure, and lyophilized to give 2.85 g. of material.

A 0.5 g. portion of this material was dissolved in 10 ml. of a solvent consisting of water:acetonitrile:dibutylamine (80:20:0.03M, which solvent had been adjusted to pH 7.8 with phosphoric acid) by addition of dibutylamine until solution had been accomplished (final pH 8.2). The solution was applied to a 2.8×59 cm. Michel-Miller HPLPLC glass column packed with 25-40 micron LiChroprep RP-8 (from MC/B Manufacturing Chemist, Inc., Cincinnati, OH).

Using an FMl pump, the column was eluted at 4 ml./min. with the same solvent combination used for sample dissolution. The eluate was monitored at 254 nm using an ISCO Model UA-5 UV detector. Selected 10 ml. fractions were analyzed for the presence of factor G by the analytical HPLC procedure described in preceding Examples.

Fractions 54-74, inclusive, rich in factor G, were combined with fractions from two similar purifications and applied at 10 ml./min. to 100 ml. of Diaion HP-20 resin in a column (2.8×22 cm), previously equilibrated with water. The column was washed with water (300 ml.) adjusted to pH 2.5 with formic acid, until no chloride was detected in the wash by precipitation as silver chloride. Elution was performed with 0.75 L. of water:acetonitrile (6:4). The eluate was concentrated under reduced pressure and lyophilized to give 960 mg. of factor G.

EXAMPLE 10

Sample Preparation for Biological Assay and Quantitative Analysis of A41030 Factor A in Dried Whole Broth One liter of whole broth was concentrated to a volume of 200 ml. and lyophilized to give 31.5 g. of dried whole broth. A 400 mg. sample of the dried whole broth was extracted 3 times with 10 ml. portions of water at pH 8.5. The extracts were combined, concentrated to a volume of 10 ml., and portions of this concentrate used for biological assay. The turbidimetric assay was conducted on a semiautomated system (Autoturb ® microbiological assay system, Elanco) described by N. R. Kuzel and F. W. Kavanaugh in J. Pharmaceut. Sci. 60(5), 764 and 767 (1971). In testing the A41030 complex, the following test parameters were used: *Staphylococcus aureus* ATCC 9144 in a nutrient broth medium (pH 7), incubated for four hours at 37° C. Test samples and standard were dissolved in methanol:water (1:1). The standard, A41030 factor A, was presented to the Autoturb ® carrousel at concentrations of 0.4, 0.6, 0.9, 1.2, and 1.5 mcg./ml.

One milliliter of the above concentrate was purified by the following procedure to be used for analysis by HPLC.

(a) One C-18 SEP-PACK cartridge was washed with 10 ml. of methanol, using a 10 ml. syringe with a Luer fitting, as known to the art.

(b) Wash the same cartridge with 10 ml. of water.

(c) Apply 1 ml. of the concentrate from above to the cartridge at the rate of approximately 1 ml./min.

(d) Wash the cartridge with 1 ml. of water and blow the cartridge dry.

(e) Elute the cartridge with 1 ml. of a solution of tetrahydrofuran:water (1:1) at about 0.5 ml./min.

(f) Remove the tetrahydrofuran from the eluate in vacuo, or alternatively, under a nitrogen stream, and reconstitute the eluate to a volume of 1 ml. with water.

(g) Analyze the solution by HPLC procedure as described hereinbefore.

The results of the assay for biological activity and the HPLC analysis of the whole broth are recorded in Table 25, which follows.

TABLE 25

| | Biological Activity and HPLC Analysis of A41030A in Whole Broth | | | |
|---|---|---|---|---|
| Sample No. | Wt. | Concentr. of A41030A+ | Total Wt. of Activity* | Total Wt. of A41030A | % of A41030A+ |
| 1 | 106.8 kg | 4.42 mg/g | 491 g | 472 g | 96.1 |
| 2 | 146.5 kg | 10.8 mg/g | 1685 g | 1582 g | 93.9 |

*Total biological activity comprised of A41030 factors A, B, C, D, E, F and G.
+As determined by HPLC.

We claim:

1. A41030 factor A, which has the structure

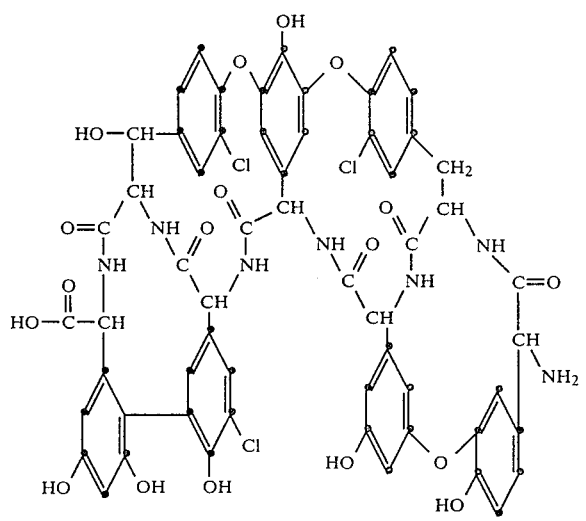

and the pharmaceutically-acceptable, non-toxic salts thereof.

2. A41030 factor B, which has the structure

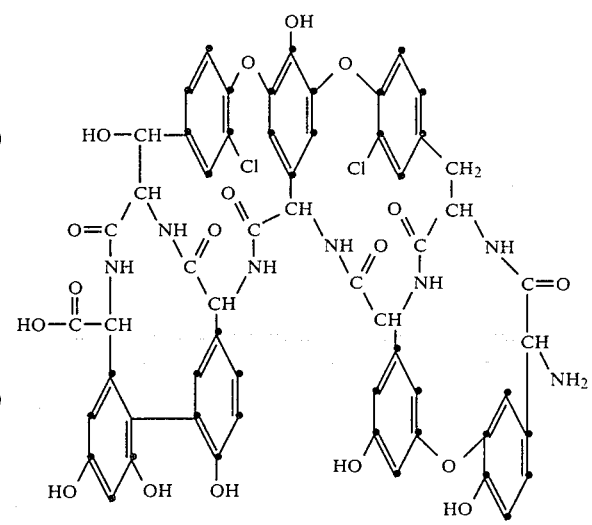

and the pharmaceutically-acceptable, non-toxic salts thereof.

3. A41030 factor C, which has the structure

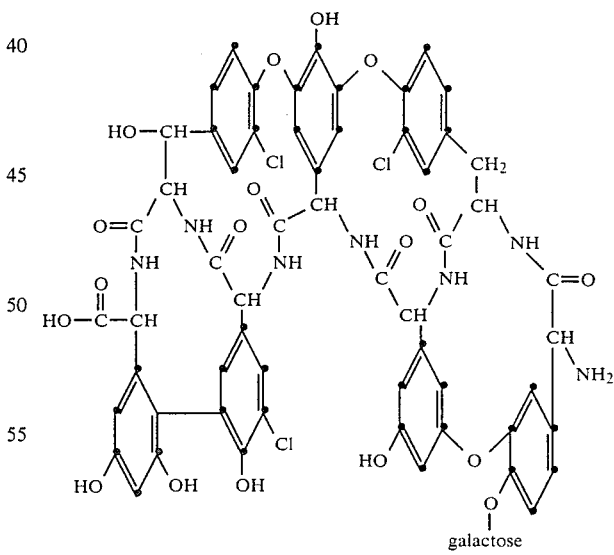

and the pharmaceutically-acceptable, non-toxic salts thereof.

4. A41030 factor E, which has the structure

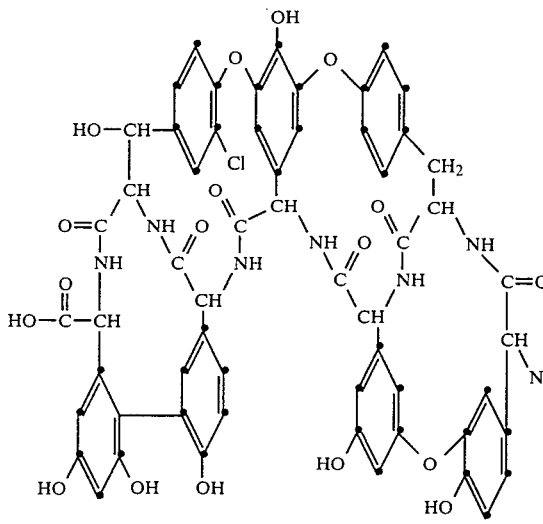

and the pharmaceutically-acceptable, non-toxic salts thereof.

5. Antibiotic A41030 factor D, which is a white, amorphous solid, having:
  (a) an approximate elemental analysis of 54.46% carbon, 4.35% hydrogen, 7.58% nitrogen, 4.27% chlorine, and by difference, 29.34% oxygen;
  (b) an observed molecular weight of about 1326, as determined by fast atom bombardment mass spectrometry;
  (c) an infrared absorption spectrum having the following distinguishable maxima: 3448–3226 (strong, broad), 2959 (weak), 1661 (strong), 1592 (strong), 1511 (strong), 1429 (weak), 1290 (weak), 1227 (weak), 1212 (medium), 1163 (weak), 1143 (weak), 1053 (medium), and 1010 (strong) cm$^{-1}$;
  (d) ultraviolet absorption spectra with an absorption maximum, in acidic and neutral methanol:water (1:1), at 278 nm ($\epsilon$ 10,600) and, in basic methanol:water (1:1), at 298 nm ($\epsilon$ 19,900);
  (e) two titratable groups in 66% aqueous dimethylformamide with pK$_a$ values of about 5.5 and 7.6;
  (f) is soluble in alcohol-water mixtures, in dimethylsulfoxide, in dimethylformamide, in dimethylsulfoxide-water mixtures, in dimethylformamide-water mixtures, in dilute aqueous acid, and in dilute aqueous base; and
  (g) the pharmaceutically-acceptable, non-toxic salts of said A41030 factor D.

6. Antibiotic A41030 factor F, which is a white solid having:
  (a) an approximate elemental analysis of 51.39% carbon, 3.96% hydrogen, 6.45% nitrogen, 6.45% chlorine, and 28.65% oxygen;
  (b) an observed molecular weight of about 1555, as determined by fast atom bombardment mass spectrometry;
  (c) an empirical formula in the range of $C_{70}H_{64}Cl_3N_7O_{28}$ based on elemental analysis and observed molecular weight;
  (d) an infrared absorption spectrum having the following distinguishable absorption maxima: 3448–3226 (strong, broad), 1653 (strong), 1600 (medium), 1504 (strong), 1429 (weak), 1258 (weak), 1227 (strong), 1136 (strong), 1075 (strong), 1053 (strong), and 1010 (strong) cm$^{-1}$;
  (e) ultraviolet absorption spectra with an absorption maximum, in acidic and neutral methanol:water (1:1), at 278 nm ($\epsilon$ 9,300) and, in basic methanol:water (1:1), at 298 nm ($\epsilon$ 14,500);
  (f) two titratable groups in 66% aqueous dimethylformamide with pK$_a$ values of about 5.4 and 7.1;
  (g) is soluble in alcohol-water mixtures, in dimethylsulfoxide, in dimethylformamide, in dimethylsulfoxide-water mixtures, in dimethylformamide-water mixtures, in dilute aqueous acid, and in dilute aqueous base; and
  (h) the pharmaceutically-acceptable, non-toxic salts of said A41030 factor F.

7. Antibiotic A41030 factor G, which is a white solid having:
  (a) an approximate elemental analysis of 50.02% carbon, 4.61% hydrogen, 4.74% chlorine, 6.11% nitrogen, and 30.70% oxygen;
  (b) an observed molecular weight of about 1684, as determined by fast atom bombardment mass spectrometry;
  (c) an empirical formula of $C_{78}H_{83}Cl_3N_8O_{28}$, based on elemental analysis and observed molecular weight;
  (d) an infrared absorption spectrum having the following distinguishable absorption maxima: 3320 (very broad, strong), 2975 (sharp, weak), 2920 (sharp, weak), 1659 (normal, strong), 1594 (broad, strong), 1512 (sharp, strong), 1492 (shoulder), 1430 (sharp, weak), 1386 (broad, weak), 1337 (broad, weak), 1308 (sharp, weak), 1264 (sharp, weak), 1230 (broad, medium), 1145 (broad, medium), 1077 (sharp, medium), 1062 (sharp, medium), 1014 (sharp, medium), and 846 (broad, medium) cm$^{-1}$;
  (e) ultraviolet absorption spectra with an absorption maximum, in acidic and neutral methanol:water (1:1), at 278 nm ($\epsilon$ 15,000) and, in basic methanol:water (1:1), at 298 nm ($\epsilon$ 18,000);
  (f) two titratable groups in 66% aqueous dimethylformamide with pK$_a$ values of about 5.4 and 7.0;
  (g) is soluble in alcohol-water mixtures, in dimethylsulfoxide, in dimethylformamide, in dimethylsulfoxide-water mixtures, in dimethylformamide-water mixtures, in dilute aqueous acid, and in dilute aqueous base; and
  (h) the pharmaceutically-acceptable, non-toxic salts of said A41030 factor G.

\* \* \* \* \*